(12) United States Patent
Conrad et al.

(10) Patent No.: US 7,541,188 B2
(45) Date of Patent: Jun. 2, 2009

(54) SKIN SUBSTITUTES AND USES THEREOF

(75) Inventors: Paul Barth Conrad, Madison, WI (US); Cathy Ann-Rusmussen Ivarie, Marshall, WI (US); Lynn Allen-Hoffmann, Madison, WI (US)

(73) Assignee: Stratatech Corporation, Madison, WI (US)

(*) Notice: Subject to any disclaimer, the term of this patent is extended or adjusted under 35 U.S.C. 154(b) by 0 days.

(21) Appl. No.: 11/006,014

(22) Filed: Dec. 7, 2004

(65) Prior Publication Data

US 2005/0226853 A1 Oct. 13, 2005

Related U.S. Application Data

(62) Division of application No. 10/087,641, filed on Mar. 1, 2002, now Pat. No. 6,846,675.

(60) Provisional application No. 60/287,898, filed on May 1, 2001, provisional application No. 60/273,034, filed on Mar. 2, 2001.

(51) Int. Cl.
  *C12N 5/00* (2006.01)
  *C12N 5/02* (2006.01)
  *C12N 5/08* (2006.01)
(52) U.S. Cl. .................. 435/404; 435/325; 435/371; 435/405; 435/407
(58) Field of Classification Search ............... 435/325, 435/404, 405, 407, 371
See application file for complete search history.

(56) References Cited

U.S. PATENT DOCUMENTS

| | | | |
|---|---|---|---|
| 4,485,096 A | 11/1984 | Bell | 424/95 |
| 5,536,656 A | 7/1996 | Kemp et al. | 435/240.23 |
| 5,618,682 A | 4/1997 | Scheirer | 435/8 |
| 5,658,331 A | 8/1997 | Della Valle et al. | 623/15 |
| 5,674,713 A | 10/1997 | McElroy et al. | 435/69.7 |
| 5,693,332 A | 12/1997 | Hansbrough | 424/426 |
| 5,712,163 A * | 1/1998 | Parenteau et al. | 435/405 |
| 5,968,546 A | 10/1999 | Baur et al. | 424/444 |
| 5,976,796 A | 11/1999 | Szalay et al. | 435/6 |
| 5,989,837 A | 11/1999 | Allen-Hoffmann et al. | 435/7.21 |
| 5,994,115 A | 11/1999 | Meyers | 435/235.1 |
| 6,039,760 A | 3/2000 | Eisenberg | 623/15 |
| 6,074,859 A | 6/2000 | Hirokawa et al. | 435/189 |
| 6,479,072 B1 * | 11/2002 | Morgan et al. | 424/443 |

OTHER PUBLICATIONS

Sando et al., J. Biol. Chem., 271(36): 22044-51 (1996).
Watanabe et al., J. Biol. Chem., 273(16): 9651-5 (1998).
Ponec et al., J. Invest. Dermatol., 109(3): 348-55 (1997).
Denda et al., J. Invest. Dermatol., 111(5): 858-63 (1998).
Hanley et al., J. Clin. Invest., 100(3): p. 705-12 (1997).
Hanley et al., J. Invest. Dermatol., 113(5): 788-95 (1999).
Anderson and Young, Quantitative Filter Hybridization, in Nucleic Acid Hybridization [1985]. This reference is a book and is not being supplied at this time. If you Examiner requests it, it will be supplies at that time.
Smith and Waterman, Adv. Appl. Math. 2: 482 (1981).
Needleman and Wunsch, J. Mol. Biol. 48:443 (1970).
Pearson and Lipman, Proc. Natl. Acad. Sci. (U.S.A.) 85:2444 (1988).
Graham and van der Eb, Virol., 52:456 [1973].
de Wet et al., Mol. Cell. Biol. 7:725 [1987].
Fuchs, J. Cell. Sci. Suppl., 17: 197-208 (1993).
Aeschlimann et al., Thrombosis & Haemostasis, 71(4): 402-15 (1994).
Reichert et al., *The cornified envelope: a key structure of terminally differentiating keratinocytes*, in Molecular Biology of the Skin, M. Darmon, Editor. 1993, Academic Press, Inc.: San Diego. 107-150 (1993).
Sachsenmeier et al., J. Biol. Chem., 271: 5-8 (1996).
Hines et al., Promega Notes, 59: p. 30-36 (1996).
Hines et al., J. Biol. Chem., 271(11): 6245-6251 (1996).
Polakowska et al., Developmental Dynamics, 199(3): 176-88 (1994).
Haake et al., J. Invest. Derm. Symp. Proc., 3: 28-35 (1998).
Wertz et al., Chem. Phys. Lipids., 91(2): 85-96 (1998).
Behne et al., J. Invest. Dermatol., 114(1): 185-92 (2000).
Auger et al., In Vitro Cell. Dev. Biol.—Animal 36:96-103.
Asbill et al., Pharm. Research 17(9): 1092-97 (2000).
Meana et al., Burns 24:621-30 (1998).
Baden, In Vitro Cell. Dev. Biol. 23(3):205-213 (1987).
Boucamp et al., J. cell. Boil. 106:761-771 (1988).
Allen-Hoffmann et al., J. Invest. Dermatol., 114(3): 444-455 (2000).
Mak et al., J. Invest. Dermatol., 96(3): 323-7 (1991).
Grubauer et al., J. Lipid Res., 30(3): 323-33 (1989).
Williams et al., J Investig. Dermatol. Symp. Proc., 3(2): 75-9 (1998).
Vicanova et al., J. Investig. Dermatol. Symp. Proc., 3(2): 114-20 (1998).
Aszterbaum et al., Pediatr. Res., 31(4 Pt 1): 308-17 (1992).
Hardman et al., Development, 125: 1541-1552 (1998).
Zhang et al., J. Biol. Chem., 273(28): 17917-25 (1998).
Denyer et al., Drug Discov. Today 3:323-32 (1998).
Gonzales et al., Drug. Discov. Today 4:431-39 (1999).
Schroeder and Neagle, J. Biomol. Screening 1:75-80 (1996).
de Brugerolle de Fraissinette et al., Cell Biology and Toxicology, 15:121 [1999].
Mukaida et al., J. Immunology, 143:1366 [1989].
Chang et al., Am J. Respir Cell Mol Biol. 22:502 [2000].
Stryer ed., *Biochemistry*, p. 17-21, 2nd ed, WH Freeman and Co., 1981.
Abe et al., Am J. Respir Cell Mol Biol., 22:51 [2000].
Roebuck, J. Interferon Cytokine Res., 19:429 [1999].
Iyer et al., Science 283:83 [1999].

(Continued)

*Primary Examiner*—Ruth A Davis
(74) *Attorney, Agent, or Firm*—Casimir Jones, S.C.

(57) ABSTRACT

The present invention relates to in vitro cultured skin substitutes, and in particular to improved methods for organotypic culture of skin substitutes. In some embodiments, the dermal equivalent of the skin substitute is lifted to air interface of the culture prior to seeding with keratinocytes. In other embodiments, increased concentrations of collagen are used to form the dermal equivalent. In still other embodiments, optimized media are utilized to maintain the skin equivalents.

4 Claims, 4 Drawing Sheets

OTHER PUBLICATIONS

Fambrough et al., Cell 97:727 [1999].
Eisen et al., PNAS 95:14863 [1998].
Golub et al., Science 286:531 [1999].
Myers et al., A. J. Surg. 170(1):75-83 (1995).
Boyce et al., Invest. Dermatol., 107(1): p. 82-7 (1996).
Shields et al., J. Biol. Chem, 271(33): 20009-17 (1996).
Geiman et al., Nucleic Acids Res., 28(5): 1106-1113 (2000).
Mahatan et al., Nucleic Acids Res., 27(23): 4562-9 (1999).
Carroll et al., Proc. Natl. Acad. Sci. USA, 90(21): p. 10270-4 (1993).
Lee et al., J. Biol. Chem., 271(8): 4561-8 (1996).
Yet et al., J. Biol. Chem., 273(2): 1026-31 (1998).
Lopez-Bayghen et al., J. Biol. Chem., 271(1): 512-520 (1996).
Furutani et al., Nuc. Acid Res. 14:3167 [1986].
Mori and Prager, Blood 87:3410 [1996].
Corsini et al., J. Invest Dermatol. 108:892 [1997].
Elefanty et al., Proc Natl Acad Sci U S A, 95:11897 [1998].
Morrison et al., Mech Dev, 1999. 84169 [1999].
Jin et al., Biochem Biophys Res Commun, 270:978 [2000].
Schurer et al., Dermatologica, 183: 77-94 (1991).
Bell et al., Proc. Nat. Acad. Sci. USA, 76: 1274-1278 (1979).
Fusenig, *Epithelial-mesenchymal interactions regulate keratinocyte growth and differentiation in vitro* in *The Keratinocyte Handbook*, I.M. Leigh, Lane, E.B., and F.M. Watt, Editor. 1994, University Press: Cambridge (1994).
Parenteau et al., Cytotechnology, 9: 163-171(1992).
Cumpstone et al., J. Invest. Dermatol., 92(4): 598-600 (1989).
Ponec, Int. J. Cosmetic Sci., 14: 245-264 (1992).
Segre et al., Nat. Genet., 22(4): 356-60 (1999).
Perkins et al., Toxicological Sciences, 48:218 [1999].
Vicanova et al., J. Invest. Dermatol., 3:97-106 (1998).
Ponec et al., Arch Dermatol Res. 289:317-326 (1997).
Stark et al., J. Invest. Dermatol. 112:681-691 (1999).
Godwin et al., J. Pharm. Sciences 86:1001-1005 (1997).
Capon et al., Cryobiology 36:174-183 (1998).
Schoop et al., J. Invest. Dermatol. 112:343-353 (1999).
Meana et al., Elsevier 24:621-630 (1998).
Horch et al., Tissue Engineering 6:53-67 (2000).
Medalie et al., Composite Skin Grafts ASAIO Journal Sept. Oct; 42(5) MS55-62 (1996).
Boyce et al., Excerpta Medica, Amer. J. of Surgery 183:445-456 (2002).
Parenteau, Keratinocyte Methods, 45-54 (1994).
Medalie et al., J. INvest. Dermatol. 107:121-127 (1996).
Wilkins et al., Biotechnology and Bioengineering 43:747-756 (1994).
Tuan et al., J. of Cell Science 107:2285-2289 (1994).
Johnson et al., In Vitro Cell. Dev. Biol. 28A:429-435 (1992).
MacCallum et al., Skin Pharmacol 3:86-96 (1990).
Lillie et al., J. of Invest. Dermatol. 90:100-109 (1988).
Krejci et al., J. Invest. Dermatol. 97:843-848 (1991).
Bouvard et al., Biochem. Cell Biol. 70:34-42 (1992).
Eaglstein et al., Advances In Wound Care, http://www.woundcarenet.com 1-7.
Regnier et al., Med. Biol. Eng. Comput., 36:821-824 (1998).
Nakazawa et al., Med. Biol. Eng. Comput., 36:813-820 (1998).
Boelsma et al., J. Invest. Dermatol. 112:489-498 (1999).

* cited by examiner

Figure 1. Mouse Klf4 DNA sequence (SEQ ID NO: 1)

```
   1 gacgccaaga gagcgagcgc ggctccgggc gcgcggggag cagaggcggt ggcgggcggc
  61 gggggcaccc ggagccgccg agtgcccctc cccgcccctc cagcccccca cccaggaacc
 121 cgcccgtgac ccgcgcccat ggccgcgcgc acccggtaca gtccccagga ctccgcaccc
 181 cgcgccaccg tccagctcgc agttccgcgc caccgcggcc attctcacct ggcggcgccg
 241 cccgccaccg cccggaccac agccccgcg ccgccgacag ccacagtggc cgcgacaacg
 301 gtgggggaca ctgctgagtc caagagcgtg cagcctggcc atcggaccta cttatctgcc
 361 ttgctgattg tctattttta taagagttta caacttttct aagaattttt gtatacaaag
 421 gaactttttt taaagacatc gccggtttat attgaatcca aagaagaagg atctcgggca
 481 atctgggggt tttggtttga ggttttgttt ctaaagtttt taatcttcgt tgactttggg
 541 gctcaggtac ccctctctct tcttcggact ccggaggacc ttctgggccc ccacattaat
 601 gaggcagcca cctggcgagt ctgacatggc tgtcagcgac gctctgctcc cgtccttctc
 661 cacgttcgcg tccggcccgg cgggaaggga gaagacactg cgtccagcag gtgccccgac
 721 taaccgttgg cgtgaggaac tctctcacat gaagcgactt cccccacttc ccggccgccc
 781 ctacgacctg gcggcgacgg tggccacaga cctggagagt ggcggagctg gtgcagcttg
 841 cagcagtaac aacccggccc tcctagcccg gagggagacc gaggagttca acgacctcct
 901 ggacctagac tttatccttt ccaactcgct aacccaccag gaatcggtgg ccgccaccgt
 961 gaccacctcg gcgtcagctt catcctcgtc ttccccggcg agcagcggcc ctgccagcgc
1021 gccctccacc tgcagcttca gctatccgat ccgggccggg ggtgaccggg gcgtggctgc
1081 cagaaacaca ggtggagggc tcctctacag ccgagaatct gcgccacctc ccacggcccc
1141 cttcaacctg ggggacatca atgacgtgag cccctcgggc ggcttcgtgg ctgagctcct
1201 gcggccggag ttggacccag tatacattcc gccacagcag cctcagccgc caggtggggg
1261 gctgatgggc aagtttgtgc tgaaggcgtc tctgaccacc cctggcagcg agtacagcag
1321 cccttcggtc atcagtgtta gcaaaggaag cccagacggc agccacccg tggtagtggc
1381 gccctacagc ggtggcccgc cgcgcatgtg cccaagatt aagcaagagg cggtcccgtc
1441 ctgcacggtc agccggtccc tagaggccca tttgagcgct ggaccccagc tcagcaacgg
1501 ccaccggccc aacacacacg acttccccct ggggcggcag ctccccacca ggactacccc
1561 tacactgagt cccgaggaac tgctgaacag cagggactgt caccctggcc tgcctcttcc
1621 cccaggattc catccccatc cgggggccaa ctacctcct ttcctgccag accagatgca
1681 gtcacaagtc ccctctctcc attatcaaga gctcatgcca ccgggttcct gcctgccaga
1741 ggagcccaag ccaaagaggg gaagaaggtc gtggccccgg aaaagaacag ccaccacac
1801 ttgtgactat gcaggctgtg gcaaaaccta taccaagagt tctcatctca aggcacacct
1861 gcgaactcac acaggcgaga aaccttacca ctgtgactgg gacggctgtg ggtggaaatt
1921 cgcccgctcc gatgaactga ccaggcacta ccgcaaacac acagggcacc ggcccttca
1981 gtgccagaag tgtgacaggg ccttttccag gtcggaccac cttgccttac acatgaagag
2041 gcacttttaa atcccacgta gtggatgtga cccacactgc caggagagag agttcagtat
2101 tttttttttct aacctttcac actgtcttcc cacgagggga ggagcccagc tggcaagcgc
2161 tacaatcatg gtcaagttcc cagcaagtca gcttgtgaat ggataatcag gagaaaggaa
2221 gagtccaaga gacaaaacag aaatactaaa aacaaacaaa caaaaaaaca aacaaaaaaa
2281 ccaagaaaaa aaaatcacag aacagatggg gtctgatact ggatggatct tctatcattc
2341 caataccaaa tccaacttga acatgcccgg acttacaaaa tgccaagggg tgactggaag
2401 tttgtggata tcagggtata cactaaatca gtgagcttgg gggagggaa gaccaggatt
2461 cccttgaatt gtgtttcgat gatgcaatac acacgtaaag atcaccttgt atgctctttg
2521 ccttcttaaa aaaaaaagc cattattgtg tcggaggaag aggaagcgat tcaggtacag
2581 aacatgttct aacagcctaa atgatggtgc ttggtgagtt gtggtcctaa aggtaccaaa
2641 cgggggagcc aaagtctcc aactgctgca tacttttgac aaggaaaatc tagtttttgtc
2701 ttccgatcta cattgatgac ctaagccagg taaataagcc tggtttattt ctgtaacatt
2761 tttatgcaga cagtctgtta tgcactgtgg tttcagatgt gcaataattt gtacaatggt
2821 ttattcccaa gtatgccttt aagcagaaca aatgtgtttt tctatatagt tccttgcctt
2881 aataaatatg taatataaat ttaaccca
```

Figure 2. DNA sequence for Human GKlf4 (SEQ ID NO:2)

```
1   tcgaggcgac cgcgacagtg gtgggggacg ctgctgagtg gaagagagcg cagcccggcc
61  accggaccta cttactcgcc ttgctgattg tctattttg cgtttacaac ttttctaaga
121 acttttgtat acaaaggaac ttttaaaaa agacgcttcc aagttatatt taatccaaag
181 aagaaggatc tcggccaatt tggggttttg ggttttggct tcgtttcttc tcttcgttga
241 ctttggggtt caggtgcccc agctgcttcg ggctgccgag gaccttctgg gcccccacat
301 taatgaggca gccacctggc gagtctgaca tggctgtcag cgacgcgctg ctcccatctt
361 tctccacgtt cgcgtctggc ccggcgggaa gggagaagac actgcgtcaa gcaggtgccc
421 cgaataaccg ctggcgggag gagctctccc acatgaagcg acttccccca gtgcttcccg
481 gccgcccta tgacctggcg gcggcgaccg tggccacaga cctggagagc ggcggagccg
541 gtgcggcttg cggcggtagc aacctggcgc ccctacctcg gagagagacc gaggagttca
601 acgatctcct ggacctggac tttattctct ccaattcgct gacccatcct ccggagtcag
661 tggccgccac cgtgtcctcg tcagcgtcag cctcctcttc gtcgtcgccg tcgagcagcg
721 gccctgccag cgcgccctcc acctgcagct tcacctatcc gatccgggcc gggaacgacc
781 cgggcgtggc gccgggcggc acgggcggag gcctcctcta tgcagggag tccgctcccc
841 ctccgacggc tcccttcaac ctggcggaca tcaacgacgt gagcccctcg ggcggcttcg
901 tggccgagct cctgcggcca gaattggacc cggtgtacat tccgccgcag cagccgcagc
961 cgccaggtgg cgggctgatg ggcaagttcg tgctgaaggc gtcgctgagc gccctggca
1021 gcgagtacgg cagcccgtcg gtcatcagcg tcagcaaagg cagccctgac ggcagccacc
1081 cggtggtggt ggcgccctac aacggcgggc cgccgcgcac gtgccccaag atcaagcagg
1141 aggcggtctc ttcgtgcacc cacttgggcg ctggacccc tctcagcaat ggccaccggc
1201 cggctgcaca cgacttcccc ctggggcggc agctccccag caggactacc ccgacctgg
1261 gtcttgagga agtgctgagc agcagggact gtcaccctgc cctgccgctt cctcccggct
1321 tccatcccca cccggggccc aattaccat ccttcctgcc cgatcagatg cagccgcaag
1381 tcccgccgct ccattaccaa gagctcatgc cacccggttc ctgcatgcca gaggagccca
1441 agccaaagag gggaagacga tcgtggcccc ggaaaaggac cgccacccac acttgtgatt
1501 acgcgggctg cggcaaaacc tacacaaaga gttcccatct caaggcacac ctgcgaaccc
1561 acacaggtga aaaccttac cactgtgact gggacggctg tggatggaaa ttcgcccgct
1621 cagatgaact gaccaggcac taccgtaaac acacggggca ccgcccgttc cagtgccaaa
1681 aatgcgaccg agcattttcc aggtcggacc acctcgcctt acacatgaag aggcattttt
1741 aaatcccaga cagtggatat gacccacact gccagaagag aattcagtat ttttactt
1801 tcacactgtc ttcccgatga gggaaggagc ccagccagaa agcactacaa tcatggtcaa
1861 gttcccaact gagtcatctt gtgagtggat aatcaggaaa aatgaggaat ccaaaagaca
1921 aaaatcaaag aacagatggg gtctgtgact ggatcttcta tcattccaat tctaaatccg
1981 acttgaatat tcctggactt acaaaatgcc aagggggtga ctggaagttg tggatatcag
2041 ggtataaatt atatccgtga gttggggag ggaagaccag aattcccttg aattgtgtat
2101 tgatgcaata taagcataaa agatcacctt gtattctctt taccttctaa aagccattat
2161 tatgatgtta gaagaagagg aagaaattca ggtacagaaa acatgtttaa atagcctaaa
2221 tgatggtgct tggtgagtct tggttctaaa ggtaccaaac aaggaagcca aagttttcaa
2281 actgctgcat acttgacaa ggaaaatcta tatttgtctt ccgatcaaca tttatgacct
2341 aagtcaggta atatacctgg tttacttctt tagcattttt atgcagacag tctgttatgc
2401 actgtggttt cagatgtgca ataatttgta caatggttta tcccaagta tgccttaagc
2461 agaacaaatg tgtttttcta tatagttcct tgccttaata aatatgtaat ataaatttaa
2521 gcaaacgtct attttgtata tttgtaaact acaaagtaaa atgaacattt tgtggagttt
2581 gtattttgca tactcaaggt gagaattaag ttttaaataa acctataata ttttatctg
```

SKIN SUBSTITUTES AND USES THEREOF

This is a divisional application of U.S. patent application Ser. No. 10/087,641, filed Mar. 1, 2002 now U.S. Pat. No. 6,846,675, which claims priority to U.S. provisional patent application Ser. Nos. 60/287,898, filed May 1 2001, and 60/273,034, filed Mar. 2 2001, the specifications of which are herin incorporated by reference in its entireties.

This patent application was supported in part by NIH SBIR grants 1 R43 AR47499-01 and 1 R43 ES10692-01A1. The government has certain rights in the invention.

FIELD OF THE INVENTION

The present invention relates to in vitro cultured skin substitutes, and in particular to in vitro cultured skin substitutes that have improved barrier function. In some embodiments, improved barrier function is a result of improved culture conditions, while in other embodiments, improved barrier function results from genetic modification of keratinocytes. The present invention further relates to the use of such skin substitutes for irritancy testing.

BACKGROUND OF THE INVENTION

There is a large market for test products and services that can predict effects of skin barrier function. There is a particular need for validated assays that would enable companies with early stage compounds to test for barrier function without resorting to expensive animal and human patch testing. Cosmetic companies spend approximately $50 million to $100 million per year on this type of testing. Household product and pharmaceutical companies make similar expenditures.

Furthermore, there is a substantial market for products for burn therapy and for the repair or support of appropriate epithelial tissues and other wound and skin closure uses. For example, venous leg ulcers affect about 1 million people in the United States and 3 million worldwide, and other ulcer conditions such as diabetic ulcers and pressure ulcers (bed-sores), affect approximately 10 million people worldwide. Venous ulcer standard care can take over 6 months to heal a wound and cost in excess of $10,000.00. Furthermore, foot ulcers are a leading cause of hospitalization among diabetics and are estimated to cost the U.S. healthcare system over $1 billion annually. Estimates for hospitalizations for burns in the United States range from 60,000 to 80,00 annually, and costs for recovery from acute injuries range from $36,000 to $117,000 per patient.

A major function of human skin is to provide a barrier to transcutaneous water loss and a barrier to prevent entry of toxic compounds or microorganisms. Development of the epidermal permeability barrier requires the coordinated synthesis and metabolism of keratinocyte-specific protein and lipid products that are assembled into the outermost skin layer, the stratum corneum. The expression of many of the key enzymes required for synthesis of these extracellular lipids is up-regulated during keratinocyte differentiation or following disruption of epidermal barrier function, suggesting the existence of transcription factors that function to promote barrier function development (Sando et al., J. Biol. Chem., 271(36): 22044-51 (1996); Watanabe et al., J. Biol. Chem., 273(16): 9651-5 (1998)). Barrier function is impaired by exposure to irritating substances, by infection and by a number of diseases including atopic dermatitis and psoriasis. Environmental stresses can exacerbate the effects of these conditions on the essential barrier function of the skin. Many industries are interested in what effect their product has on barrier function of the skin. For example, companies that deliver pharmaceuticals transdermally need to facilitate the penetration of the active agent past the barrier. Cosmetic companies are interested in finding formulations that improve the barrier function.

In order to test compounds or formulations early in the development process with speed and accuracy, it would be beneficial to have an in vitro test system that mimics the barrier properties of human skin. However, published studies indicate that existing skin equivalent cultures, such as EPI-DERM, SKINETHICS or EPISKIN, have very poor barrier function (Ponec et al., J. Invest. Dermatol., 109(3): 348-55 (1997)). There has been substantial recent progress, however, in understanding the importance of vitamin C, nuclear hormone receptors, lipid synthesis, and humidity on the proper development of barrier function (Ponec et al., J. Invest. Dermatol., 109(3): 348-55 (1997); Denda et al., J. Invest. Dermatol., 111(5): 858-63 (1998); Hanley et al., J. Clin. Invest., 100(3): p. 705-12 (1997); Hanley et al., J. Invest. Dermatol., 113(5): 788-95 (1999)). In many cases, these studies focus on chemical or environmental signals that trigger the natural developmental program that establishes barrier function at a specific time in utero. Clearly, a great need exists for skin substitutes having improved barrier function.

SUMMARY OF THE INVENTION

The present invention relates to in vitro cultured skin substitutes, and in particular to in vitro cultured skin substitutes that have improved barrier function. In some embodiments, improved barrier function is a result of improved culture conditions, while in other embodiments, improved barrier function results from genetic modification of keratinocytes. The present invention further relates to the use of such skin substitutes for irritancy testing.

The present invention provides compositions comprising a human skin equivalent, the skin equivalent having a surface electrical capacitance of from about 40 to about 240 pF. In some preferred embodiments, the skin equivalent has a surface electrical capacitance of from about 80 to about 120 pF. In other preferred embodiments, the combined content of ceramides 5, 6, and 7 in the skin equivalent is from about 20 to about 50% of total ceramide content. In still other preferred embodiments, the content of ceramide 2 in the skin equivalent is from about 10 to about 40% of total ceramide content. The present invention is not limited to skin equivalents formed from a particular source of keratinocytes. Indeed, the skin equivalents may be formed from a variety of primary and immortal keratinocytes, including, but not limited to NIKS cells. In still further embodiments, the keratinocytes express exogenous wild-type or variant GKLF. In still further embodiments, the keratinocytes are derived from two or more different sources.

In other embodiments, the present invention provides isolated keratinocytes comprising a sequence encoding GKLF operably linked to an exogenous promoter. In still further embodiments, the present invention provides an organotypic culture keratinocytes comprising a sequence encoding exogenous GKLF operably linked to an exogenous promoter.

In some embodiments, the present invention provides methods for making skin equivalents having improved barrier function. In some embodiments, the methods comprise providing keratinocytes and a culture media comprising ascorbic acid and linoleic acid; and culturing the keratinocytes under conditions such that a skin equivalent having improved barrier function is formed. In some embodiments, the culture conditions include culture at about 50 to 95% humidity, preferably about 75% humidity. In some preferred embodiments, the ascorbic acid is provided at concentration of from about 10 to 100 micrograms/ml. In still further preferred embodiments, linoleic acid is provided at a concentration of from about 5 to 80 micromolar. The present invention is not limited to skin equivalents formed from a particular source of keratinocytes. Indeed, the skin equivalents may be formed from a variety of primary and immortal keratinocytes, including, but not limited to NIKS cells. In still further embodiments, the keratinocytes express exogenous wild-type or variant GKLF. In still further embodiments, the keratinocytes are derived from two different sources. In other embodiments, the skin equivalent has a surface electrical capacitance of from about 40 to about 240 pF. In some preferred embodiments, the skin equivalent has a surface electrical capacitance of from about 80 to about 120 pF. In other preferred embodiments, the content of ceramides 5, 6, and 7 in the skin equivalent is from about 20 to about 50% of total ceramide content. In still other preferred embodiments, the content of ceramide 2 in the skin equivalent is from about 10 to about 40% of total ceramide content. In still further embodiments, the present invention provides the skin equivalent made by the method just described.

In other embodiments, the present invention provides methods of making skin equivalents having improved barrier function comprising: providing keratinocytes and a DNA construct comprising a sequence encoding GKLF operably linked to an exogenous promoter; transfecting the keratinocytes with said DNA construct to provide transfected keratinocytes; and culturing the transfected keratinocytes under conditions such that a skin equivalent having improved barrier function is formed. In some embodiments, the culturing step comprises culturing the transfected keratinocytes in a culture media comprising ascorbic acid and linoleic acid. In some preferred embodiments, the ascorbic acid is provided at concentration of from about 10 to 100 micrograms/ml. In still further preferred embodiments, linoleic acid is provided at a concentration of from about 5 to 80 micromolar. The present invention is not limited to skin equivalents formed from a particular source of keratinocytes. Indeed, the skin equivalents may be formed from a variety of primary and immortal keratinocytes, including, but not limited to NIKS cells. In still further embodiments, the keratinocytes express wild-type or variant GKLF. In still further embodiments, the keratinocytes are derived from two different sources. In other embodiments, the skin equivalent has a surface electrical capacitance of from about 40 to about 240 pF. In some preferred embodiments, the skin equivalent has a surface electrical capacitance of from about 80 to about 120 pF. In other preferred embodiments, the content of ceramides 5, 6, and 7 in the skin equivalent is from about 20 to about 50% of total ceramide content. In still other preferred embodiments, the content of ceramide 2 in the skin equivalent is from about 10 to about 40% of total ceramide content. In still further embodiments, the present invention provides the skin equivalent made by the described methods.

In still other embodiments, the present invention provides methods for screening compounds. In some embodiments, the methods comprise providing a skin equivalent having a surface electrical capacitance of from about 40 to about 240 pF; and treating the skin equivalent with said compound. In further embodiments, the method comprise step c) assaying the effect of said compound on said skin equivalent. In some preferred embodiments, the compound is selected from a combinatorial library. The present invention is not limited to skin equivalents formed from a particular source of keratinocytes. Indeed, the skin equivalents may be formed from a variety of primary and immortal keratinocytes, including, but not limited to NIKS cells. In still further embodiments, the keratinocytes express exogenous wild-type or variant GKLF. In still further embodiments, the keratinocytes are derived from two different sources. In other embodiments, the skin equivalent has a surface electrical capacitance of from about 40 to about 240 pF. In some preferred embodiments, the skin equivalent has a surface electrical capacitance of from about 80 to about 120 pF. In other preferred embodiments, the content of ceramides 5, 6, and 7 in the skin equivalent is from about 20 to about 50% of total ceramide content. In still other preferred embodiments, the content of ceramide 2 in the skin equivalent is from about 10 to about 40% of total ceramide content.

In other embodiments, the present invention provides kits comprising at least one skin equivalent having a surface electrical capacitance of from about 40 to about 240 pF. In still other embodiments, the kit includes culture media for culturing the at least one skin equivalent. In some embodiments, the kit further comprises instructions for culturing the skin equivalent. In other embodiments, the kit further comprises instructions for testing compounds using said at least one skin equivalent. The present invention is not limited to skin equivalents formed from a particular source of keratinocytes. Indeed, the skin equivalents may be formed from a variety of primary and immortal keratinocytes, including, but not limited to NIKS cells. In still further embodiments, the keratinocytes express wild-type or variant GKLF. In still further embodiments, the keratinocytes are derived from two different sources. In other embodiments, the skin equivalent has a surface electrical capacitance of from about 80 to about 120 pF. In some preferred embodiments, the skin equivalent has a surface electrical capacitance of from about 80 to about 120 pF. In other preferred embodiments, the content of ceramides 5, 6, and 7 in the skin equivalent is from about 20 to about 50% of total ceramide content. In still other preferred embodiments, the content of ceramide 2 in the skin equivalent is from about 10 to about 40% of total ceramide content.

In still further embodiments, the present invention provides a method of screening compounds suspected of being skin irritants, comprising: providing a compound suspected of being a skin irritant; a skin equivalent comprising a irritant responsive reporter gene construct; and contacting said skin equivalent with said compound; and measuring the level of gene expression from said reporter gene construct. In some embodiments, the human skin equivalent has a surface electrical capacitance of from about 80 to about 120 pF. In some embodiments, the content of ceramides 5, 6, and 7 in the skin equivalent is from about 20 to about 50% of total ceramide content. In other embodiments, the content of ceramide 2 in said skin equivalent is from about 10 to about 40% of total ceramide content. In some embodiments, the skin equivalent comprises keratinocytes selected from the group consisting of primary keratinocytes and immortalized keratinocytes. In some embodiments, the immortalized keratinocytes are NIKS cells. In other embodiments, the keratinocytes express heterologous GKLF. In yet other embodiments, the irritant responsive reporter construct comprises at least a portion of a gene selected from the group consisting of interleukin-8 and interleukin-1$\alpha$. In some preferred embodiment, the portion comprises a regulatory region.

The present invention also provides a composition comprising NIKS cells comprising an irritant responsive reporter gene construct. In some embodiments, the NIKS cells have a surface electrical capacitance of from about 40 to about 240 pF. In other embodiments, the NIKS cells have a surface electrical capacitance of from about 80 to about 120 pF. In some embodiments, the combined content of ceramides 5, 6, and 7 in the NIKS cells is from about 20 to about 50% of total ceramide content. In other embodiments, the content of ceramide 2 in said NIKS cells is from about 10 to about 40% of total ceramide content. In still further embodiments, the NIKS cells express heterologous GKLF. In some embodiments, the NIKS cells further comprise a DNA construct comprising a sequence encoding GKLF operably linked to an exogenous promoter. In yet other embodiments, the NIKS cells further comprise keratinocytes derived from two different sources. In other embodiments, the NIKS cells are present as nn organotypic culture In still other embodiments, the present invention provides a method of identifying irritant responsive genes, comprising: providing a skin irritant compound; a gene expression array; and a skin equivalent; and contacting said skin irritant compound with said skin equivalent to generate irritant treated skin equivalent; isolating a first mRNA sample from said irritant treated skin equivalent and a second mRNA sample from said skin equivalent; contacting said first and second mRNA samples with said gene expression array; analyzing said gene expression array under conditions such that the identity of genes that are expressed at greater levels in said irritant treated skin equivalent than in said skin equivalent are determined. In some embodiments, the skin equivalent comprises cultured human keratinocytes. In other embodiments, the cultured human keratinocytes are present as an organotypic culture. In some embodiments, the irritant responsive reporter construct comprises at least a portion of a gene selected from the group consisting of interleukin-8 and interleukin-1α. In some preferred embodiments, the portion comprises a regulatory region. In some embodiments, the gene array comprises human cDNA sequences.

The present invention also relates to in vitro cultured skin substitutes, and in particular to improved methods for organotypic culture of skin substitutes. In some embodiments, the present invention provides processes for preparing a seeded dermal equivalent comprising: providing a dermal equivalent, keratinocytes, and culture media having an air interface; culturing the dermal equivalent in the culture media; lifting the dermal equivalent to the air interface to provide a lifted dermal equivalent; and seeding the dermal equivalent with the keratinocytes to provide a seeded dermal equivalent. The present invention is not limited to the use of any particular type of keratinocytes. Indeed, the use of keratinocytes from a variety of sources is contemplated, including but not limited to keratinocytes selected from the group consisting of primary human keratinocytes and immortalized human keratinocytes. In some particularly preferred embodiments, the immortalized keratinocytes are NIKS cells. The present invention is not limited to the use of any particular dermal equivalent. In some preferred embodiments, the dermal equivalent comprises collagen and fibroblasts. The present invention is not limited to the use of any particular type of collagen. Indeed, the use of a variety of types of collagen is contemplated, including, but not limited to rat tail tendon collagen. Likewise, the present invention is not limited to the use of any particular type of fibroblasts. Indeed, the use of a variety of fibroblasts is contemplated, including, but not limited to, NHDF cells. In some particularly preferred embodiments, the lifting step further comprises incubating the lifted dermal equivalent at the air interface for at least six hours prior to the seeding. In other particularly preferred embodiments, the lifting step further comprises incubating the lifted dermal equivalent at the air interface for at least twelve hours prior to the seeding. In still other particularly preferred embodiments, the lifting step further comprises incubating the lifted dermal equivalent at the air interface for at least eighteen hours prior to the seeding. In still more preferred embodiments, the lifting step further comprises incubating the lifted dermal equivalent at the air interface for about 24 hours prior to the seeding. In still other preferred embodiments, the lifting step further comprises incubating the lifted dermal equivalent at the air interface for about six hours to about 24 hours prior to the seeding.

In some embodiments, the methods of the present invention further comprise the step of incubating the seeded dermal skin equivalent under conditions such that a skin equivalent is formed. In some preferred embodiments, the skin equivalent is stratified. In particularly preferred embodiments, the skin equivalent is stratified into squamous epithelia. In still further embodiments, the present invention provides seeded dermal equivalents and skin equivalents produced by the foregoing methods.

In still other embodiments, the present invention provides compositions comprising a growth chamber having a porous bottom surface and a side-wall, the porous bottom having thereon a dermal equivalent wherein the dermal equivalent is substantially adhered to the side-wall of the growth chamber. The present invention is not limited to growth chambers of any particular size. Indeed, growth chambers of a variety of sizes are contemplated. In some preferred embodiments, the porous bottom of the growth chamber is about 0.1 to 20.0 centimeters in diameter. In other preferred embodiments, the porous bottom of the growth chamber is about 1.0 centimeters in diameter. The present invention is not limited to the use of any particular dermal equivalent. In some preferred embodiments, the dermal equivalent comprises collagen and fibroblasts. The present invention is not limited to the use of any particular type of collagen. Indeed, the use of a variety of types of collagen is contemplated, including, but not limited to rat tail tendon collagen. Likewise, the present invention is not limited to the use of any particular type of fibroblasts. Indeed, the use of a variety of fibroblasts is contemplated, including, but not limited to, NHDF cells. In some embodiments, the composition further comprises keratinocytes, wherein the keratinocytes are seeded onto the dermal equivalent to form a skin equivalent. The present invention is not limited to the use of any particular type of keratinocytes. Indeed, the use of keratinocytes from a variety of sources is contemplated, including but not limited to keratinocytes selected from the group consisting of primary human keratinocytes and immortalized human keratinocytes. In some particularly preferred embodiments, the immortalized keratinocytes are NIKS cells. In some preferred embodiments, the keratinocytes are stratified. In particularly preferred embodiments, the keratinocytes are stratified into squamous epithelia.

In still further embodiments, the present invention provides a composition comprising a dermal equivalent, wherein the dermal equivalent contain about 0.2 mg collagen per square centimeter of the dermal equivalent to 2.0 mg collagen per square centimeter of the dermal equivalent. In some particularly preferred embodiments, the dermal equivalent contains about 0.22 mg collagen per square centimeter of the dermal equivalent to 1.0 mg collagen per square centimeter of the dermal equivalent. In other particularly preferred embodiments, the dermal equivalent contains about 0.5 mg collagen per square centimeter of the dermal equivalent. In some embodiments, the composition further comprises keratinocytes, wherein the keratinocytes are seeded onto the dermal equivalent to form a skin equivalent. The present invention is not limited to the use of any particular type of keratinocytes.

Indeed, the use of keratinocytes from a variety of sources is contemplated, including but not limited to keratinocytes selected from the group consisting of primary human keratinocytes and immortalized human keratinocytes. In some particularly preferred embodiments, the immortalized keratinocytes are NIKS cells. In some preferred embodiments, the keratinocytes are stratified. In particularly preferred embodiments, the keratinocytes are stratified into squamous epithelia. The present invention is not limited to the use of any particular dermal equivalent. In some preferred embodiments, the dermal equivalent comprises collagen and fibroblasts. The present invention is not limited to the use of any particular type of collagen. Indeed, the use of a variety of types of collagen is contemplated, including, but not limited to rat tail tendon collagen. Likewise, the present invention is not limited to the use of any particular type of fibroblasts. Indeed, the use of a variety of fibroblasts is contemplated, including, but not limited to, NHDF cells.

In still further embodiments, the present invention provides a composition comprising BSA, isoproterenol, carnitine, serine, oleic acid, linoleic acid, arachidonic acid, α-tocopherol, ascorbic acid, and EGF. The present invention is not limited to any particular concentration of the foregoing compounds. Indeed, the amounts of these compounds in the composition can vary. In preferred embodiments, the BSA, isoproterenol, carnitine, serine, oleic acid, linoleic acid, arachidonic acid, α-tocopherol, ascorbic acid, and EGF are present in concentrations sufficient to improve barrier function in in vitro cultured skin equivalents. In some embodiments, the composition further comprises serum. In still other embodiments, the compositions further comprise calcium chloride, hydrocortisone, cholera toxin, insulin and adenine. In preferred embodiments, the bovine serum albumin is provided at a concentration of about 0.1-10.0 mg/ml. In other preferred embodiments, the isoproterenol is provided at a concentration of about 0.1-10.0 µM. In still other preferred embodiments, the carnitine is provided at a concentration of about 1.0-100.0 µM. In further preferred embodiments, the serine is provided at a concentration of about 1.0-100.0 µM. In still further preferred embodiments, the oleic acid is provided at a concentration of about 1.0-100.0 µM. In still other preferred embodiments, the linoleic acid is provided at a concentration of about 1.0-100.0 µM. In some preferred embodiments, the arachidonic acid is provided at a concentration of about 1.0-100.0 µM. In other preferred embodiments, the α-tocopherol is provided at a concentration of about 0.1-10.0 µM. In still other preferred embodiments, the ascorbic acid is provided at a concentration of about 0.005-5.0 mg/ml. In still further preferred embodiments, the epidermal growth factor is provided at a concentration of about 0.1-10.0 ng/ml.

DESCRIPTION OF THE FIGURES

FIG. 1 is the nucleic acid sequence for mouse Klf4 (SEQ ID NO:1).

FIG. 2 is the nucleic acid sequence for human GKLF (SEQ ID NO:2)

DEFINITIONS

Figure 3:
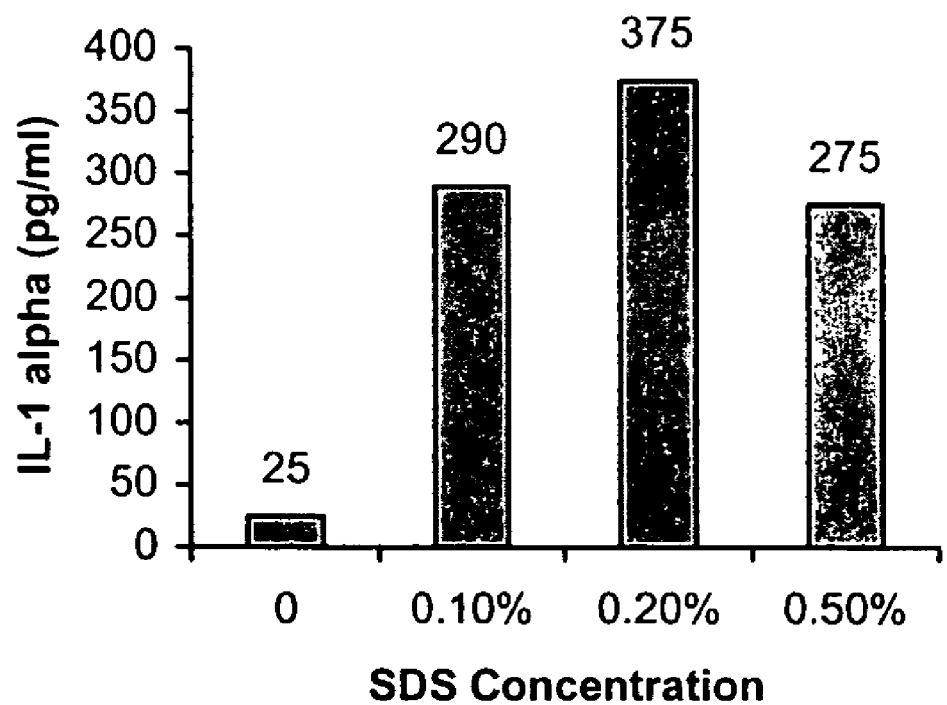
FIG. 3 shows IL-1α Secretion by NIKS organotypic cultures.

As used herein, the term "GKLF" when used in reference to a protein or nucleic acid refers to a protein or nucleic acid encoding a protein that shares greater than about 50% identity with SEQ ID NO:1 and/or SEQ ID NO:2 and binds to the basic transcription element of the cytochrome p450IAI promoter. Binding activity may be conveniently assayed by an electrophoretic mobility gel shift assay using the oligonucleotide GAGAAGGAGGCGTGGCCAAC (SEQ ID NO:3) as described in Zhang et al., J. Biol. Chem., 273(28): 17917-25 (1998). Thus, the term GKLF encompasses both proteins that are identical to wild-type GKLF and those that are derived from wild type GKLF (e.g., variants of GKLF or chimeric genes constructed with portions of GKLF coding regions).

As used herein, the term "activity of GKLF" refers to any activity of wild type GKLF. The term is intended to encompass all activities of GKLF.

As used herein, the terms "skin equivalent" and "skin substitute" are used interchangeably to refer to an in vitro-derived culture of keratinocytes that has stratified into squamous epithelia in what is termed an organotypic culture.

As used herein, the term "dermal equivalent" is used to refer to an in vitro-derived culture comprising collagen and fibroblast cells. It is contemplated that "dermal equivalents" can serve as substrates for differentiation of keratinocytes in an organotypic culture.

As used herein, the term "air interface" refers to the interface between the atmosphere and liquid medium in a culture dish.

As used herein the term "substantially adhered to a sidewall," when used in reference to a dermal equivalent, refers to the physical adherence of a dermal equivalent to a substantially vertical wall, as opposed to the dermal equivalent contracting or pulling away from the substantially vertical wall.

As used herein, the term "organotypic" culture refers to a three-dimensional tissue culture where cultured cells are used to reconstruct a tissue or organ in vitro.

As used herein, the term "NIKS cells" refers to cells having the characteristics of the cells deposited as cell line ATCC CRL-12191.

As used herein, the term "NHDF" refers to cells having the characteristics of normal human dermal fibroblasts.

As used herein, the term "content of ceramides" refers to the amount of ceramides in a skin equivalent sample as assayed by high-performance thin-layer chromatography.

As used herein, the term "skin irritant" refers to a compound that, when applied to skin or a skin equivalents, elicits a cellular response characterized by the expression of an "irritant responsive gene." Examples of known skin irritants include, but are not limited to, SDS, calcipotriol, and trans-retinoic acid. The term "skin irritant" is also intended to encompass unknown or suspected irritants, including but not limited to, those containing in some pharmaceuticals, cosmetics, and consumer products.

As used herein, the term "irritant responsive gene" refers to a gene that is expressed to a greater level (e.g., as measured by the level of mRNA expression) in the presence of a skin irritant. Examples of irritant responsive genes include, but are not limited to, Interleukin-8 and Interleukin-1α. The term "irritant responsive gene" is also intended to encompass unknown irritant responsive genes (e.g., those identified by the methods of the present invention).

The term "gene" refers to a nucleic acid (e.g., DNA) sequence that comprises coding sequences necessary for the production of a polypeptide or precursor (e.g., GKLF). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "GKLF gene" refers to the full-length GKLF nucleotide sequence (e.g., contained in SEQ ID NO:2). However, it is also intended that the term encompass fragments of the GKLF sequence, as well as other domains within the full-length GKLF nucleotide sequence. Furthermore, the terms "GKLF nucleotide sequence" or "GKLF polynucleotide sequence" encompasses DNA, cDNA, and RNA (e.g., mRNA) sequences.

As used herein, the term "gene array" refers to a solid support (e.g., a filter, a glass slide, or a microchip) to which a plurality of nucleic acid sequences are affixed. As used herein, the term "gene expression array" refers to a gene array for use in measuring the expression of genes that are contained on the array. In preferred embodiments, the nucleic acid sequences affixed to a gene expression array are cDNA sequences.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described below.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as, greater than, or less than the efficiency of substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$(% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., GKLF).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding GKLF includes, by way of example, such nucleic acid in cells ordinarily expressing GKLF where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "purified" or "to purify" refers to the removal of contaminants from a sample.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the GKLF mRNA-specific signal observed on Northern blots). The amount of mRNA present in the band corresponding in size to the correctly spliced GKLF transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding GKLF (e.g., SEQ ID NO:2) or fragments thereof may be employed as hybridization probes. In this case, the GKLF encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response", when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyl-transferase, beta-galactosidase, alkaline phosphatase, and horse radish peroxidase.

As used herein, the term "irritant responsive reporter gene construct" refers to a construct comprising a reporter gene operably linked to a regulatory region of an irritant responsive gene.

DESCRIPTION OF THE INVENTION

The present invention relates to in vitro cultured skin substitutes, and in particular to in vitro cultured skin substitutes that have improved barrier function. In some embodiments, improved barrier function is a result of improved culture conditions, while in other embodiments, improved barrier function results from genetic modification of keratinocytes. In still other embodiments, the present invention provides skin substitutes comprising reporter gene constructs (e.g., irritant responsive reporter gene constructs).

Human skin protects the body from environmental insults such as chemicals and microorganisms. It is also critical for preventing the loss of water from our bodies. Defects in skin barrier function have detrimental effects leading to entry of poisonous substances, infection or severe water loss. Sometimes it is desirable to improve the barrier function of the skin for medical, infant care or cosmetic reasons, while at other times it would be advantageous to lower the permeability barrier; to administer drugs transdermally, for example. Pharmaceutical, cosmetic and consumer product companies all have products that may come into contact with the skin. These companies need to know early in the development process whether their compound or formulation will affect the essential barrier function of the skin. Excised skin tissue has been used for measuring percutaneous absorption but a number of problems with this preparation have been noted in the literature. There are differences in absorption between human and animal skin that can result in misleading results and the availability of human tissue is variable. There are also growing political and social pressures to eliminate or reduce the number of animals being used for safety testing.

These difficulties and the growing need to understand the permeability properties of new formulations and potential transdermal therapeutics have led to many studies to improve the permeability properties of in vitro skin equivalent cultures. The development of a cultured skin substitute that recapitulates the barrier properties of human skin will also provide a better source of synthetic tissue for burn therapy. The availability of cultured skin substitutes that more closely resemble human skin will facilitate the testing of cosmetics, pharmaceuticals, and other topical compounds by reducing the reliance on animal testing of these products.

Stratified squamous epithelia, such as skin and oral epithelia, are multilayered renewal tissues composed primarily of keratinocytes. Differentiated keratinocytes are continuously lost from the surface and replaced by the proliferation of basal keratinocytes. The rate at which a basal call initiates and completes its differentiation program appears to be tightly regulated, although the molecular controls for such regulation are ill-defined (Fuchs, J. Cell. Sci. Suppl., 17: 197-208 (1993)). In vivo, the final stages of the terminal differentiation process are characterized by numerous changes including filaggrin-mediated keratin intermediate filament bundling, and release of lipids from membrane-coating granules into the intercellular space (Schurer et al., Dermatologica, 183: 77-94 (1991)). The cornified envelope, another terminal differentiation structure consisting of several proteins that are covalently crosslinked by the action of calcium-dependent transglutaminases, is also formed in differentiating keratinocytes (Aeschlimann et al., Thrombosis & Haemostasis, 71(4): 402-15 (1994); Reichert et al., *The cornified envelope: a key structure of terminally differentiating keratinocytes*, in *Molecular Biology of the Skin*, M. Darmon, Editor. 1993, Academic Press, Inc.: San Diego. 107-150 (1993)). In the epidermis, keratinocytes lose intracellular organelles and enucleate in the upper layers of the tissue, forming a "dead shell" with high tensile strength. Molecular mechanisms which govern keratinocyte enucleation and terminal differentiation are poorly understood. Studies ((Sachsenmeier et al., J. Biol. Chem., 271: 5-8 (1996); Hines et al., Promega Notes, 59: p. 30-36 (1996); Hines et al., J. Biol. Chem., 271(11): 6245-6251 (1996); Polakowska et al., Developmental Dynamics, 199(3): 176-88 (1994); Haake et al., J. Invest. Derm. Symp. Proc., 3: 28-35 (1998)) suggest that terminal differentiation in keratinocytes may constitute a special form of apoptotic cell death.

Human skin is composed of a dermal layer containing fibroblasts embedded in an extracellular protein matrix and an epidermal layer, consisting primarily of keratinocytes that differentiate to form the outermost, impermeable skin layer. The primary function of human skin is to provide a physical barrier to prevent excessive loss of bodily fluid due to evaporation. Barrier function is localized in the stratum corneum of the skin. The stratum corneum has been described as an array of impermeable keratin-filled cells embedded in a matrix of lipid, analogous to a brick wall. Critical components of the stratum corneum barrier are the lipids deposited by the keratinocytes during formation of the stratum corneum. In the stratum granulosum, keratinocytes contain keratohyalin granules and lamellar bodies. At the stratum granulosum/ stratum corneum interface, the lamellar bodies fuse with the plasma membrane and extrude their lipid contents into the intercellular space. A number of enzymes are also released which serve to process phospholipids and glucosylceramides to fatty acids and ceramides respectively. The extracellular lipids of the stratum corneum are assembled into multilamellar structures that surround the keratin-filled cornified envelopes produced from the keratinocytes. Stratum corneum lipids comprise 10-15% of the dry weight of the tissue and consist primarily (by weight) of ceramides (50%), cholesterol (25%) and free fatty acids (10%) in roughly equimolar amounts (Wertz et al., Chem. Phys. Lipids., 91(2): 85-96 (1998)). These lipids are derived principally from biosynthesis in the keratinocytes. A portion of the ceramides have the unusual role of forming covalent bonds with groups at the surface of the cornified envelopes, including bonds to involucrin. This covalently bound omega-hydroxyceramide forms a lipid monolayer surrounding the outer surface of the cornified cells. The precise role of this structure is unknown. Recently the importance of omega-hydroxyceramides on barrier function was demonstrated by inhibiting their formation in hairless mouse skin with an inhibitor of the CYP4 P-450 omega hydroxylase (Behne et al., J. Invest. Dermatol., 114(1): 185-92 (2000)).

After the discovery that ruthenium tetroxide could be used to reveal the lamellae in electron microscopy, analysis of stratum corneum ultrastructure has provided important insights into the quality of the stratum corneum. For example, studies have examined the presence of lamellar bodies in the stratum granulosum, the appropriate excretion of lamellar body contents at the stratum granulosum/stratum corneum interface and the presence of alternating electron dense and electron lucent bands of the lipid lamellae. Electron microscopy also reveals electron dense desmosomes in the stratum corneum, occupying ~15% of the intercellular spaces and possibly important in cell-cell adherence.

The present invention provides skin substitutes having improved barrier function, and compositions and methods for making skin substitutes having improved barrier function. For convenience, the description of the invention is presented in the following sections: A) Sources of Keratinocytes and Other Cells for Creating Skin Substitutes Having Improved Barrier Function; B) Culture Conditions and Methods for Creating Skin Substitutes with Improved Properties; C) Genetic Modification of Cells for Improved barrier Function; and D) Uses of Skin Substitutes having Improved Barrier Function.

A. Sources of Keratinocytes and Other Cells for Creating Skin Substitutes

It is contemplated that the methods of the present invention can be used to create skin substitutes having improved barrier function. Generally, any source of cells or cell line that can stratify into squamous epithelia are useful in the present invention. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968, 546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucanp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of these cell lines can be cultured or genetically modified as described below in order to improve barrier function of the resulting skin equivalent.

In particularly preferred embodiments, NIKS cells are utilized. The discovery of a novel human keratinocyte cell line (near-diploid immortalized keratinocytes or NIKS) provides an opportunity to genetically engineer human keratinocytes for new in vitro testing methods. A unique advantage of the NIKS cells is that they are a consistent source of genetically-uniform, pathogen-free human keratinocytes. For this reason, they are useful for the application of genetic engineering and genomic gene expression approaches to provide skin equivalent cultures with properties more similar to human skin. Such systems will provide an important alternative to the use of animals for testing compounds and formulations. The NIKS keratinocyte cell line, identified and characterized at the University of Wisconsin, is nontumorigenic, exhibits a stable karyotype, and exhibits normal differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, the immortalized NIKS cells will continue to proliferate in monolayer culture indefinitely. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies which exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescencing population were originally designated BC-1-Ep/Spontaneous Line and are now termed NIKS. The NIKS cell line has been screened for the presence of proviral DNA sequences for HIV-1, HIV-2, EBV, CMV, HTLV-1, HTLV-2, HBV, HCV, B-19 parvovirus, HPV-16 and HPV-31 using either PCR or Southern analysis. None of these viruses were detected.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. At passage 54, all cells contained the isochromosome 8.

The DNA fingerprints for the NIKS cell line and the BC-1-Ep keratinocytes are identical at all twelve loci analyzed demonstrating that the NIKS cells arose from the parental BC-1-Ep population. The odds of the NIKS cell line having the parental BC-1-Ep DNA fingerprint by random chance is $4 \times 10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium was investigated. After 4 weeks in either agar- or methylcellulose-containing medium, NIKS cells remained as single cells. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both surface culture and organotypic culture. For cells in surface culture, a marker of squamous differentiation, the formation cornified envelopes was monitored. In cultured human keratinocytes, early stages of cornified envelope assembly result in the formation of an immature structure composed of involucrin, cystatin-α and other proteins, which represent the innermost third of the mature cornified envelope. Less than 2% of the keratinocytes from the adherent BC-1-Ep cells or the NIKS cell line produce cornified envelopes. This finding is consistent with previous studies demonstrating that actively growing, subconfluent keratinocytes produce less than 5% cornified envelopes. To determine whether the NIKS cell line is capable of producing cornified envelopes when induced to differentiate, the cells were removed from surface culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS keratinocytes produced as many as and usually more cornified envelopes than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper layers of keratinocytes and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed To observe more detailed characteristics of the parental (passage 5) and NIKS (passage 38) organotypic cultures and to confirm the histological observations, samples were analyzed using electron microscopy. Parental cells and the immortalized human keratinocyte cell line, NIKS, were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted. Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the porous support. These findings are consistent with earlier ultrastructural findings using human foreskin keratinocytes cultured on a fibroblast-containing porous support. Analysis at both the light and electron microscopic levels demonstrate that the NIKS cell line in organotypic culture can stratify, differentiate, and form structures such as desmosomes, basal lamina, and hemidesmosomes found in normal human epidermis.

B. Culture Conditions and Methods for Creating Skin Substitutes with Improved Properties In some embodiments of the present invention, methods of culturing skin equivalents are provided that result in enhanced barrier function as compared to skin equivalents cultured by conventional methods. Full stratification and histological differentiation of normal keratinocytes can be achieved by the use of three-dimensional organotypic culture methods (Bell et al., Proc. Nat. Acad. Sci. USA, 76: 1274-1278 (1979); Fusenig, *Epithelial-mesenchymal interactions regulate keratinocyte growth* and *differentiation* in vitro, in *The Keratinocyte Handbook*, I. M. Leigh, Lane, E. B., and F. M. Watt, Editor. 1994, University Press: Cambridge (1994); Parenteau et al., Cytotechnology, 9: 163-171(1992)). Normal keratinocytes grown on the surface of collagen gels containing dermal fibroblasts can generate specialized structures, such as the basement membrane and hemidesmosomes, which are characteristic of the normal tissue architecture of stratified squamous epithelia. The organotypic culture technique for normal keratinocytes has fostered the recent development of in vitro models for cutaneous pharmacotoxicological studies. This has become an important alternative to animal testing.

When in vitro cultures of human keratinocytes are grown at an air-liquid interface, a highly ordered stratum corneum is formed. Although permeability to water decreases with increased culturing time at the air-liquid interface (Cumpstone et al., J. Invest. Dermatol., 92(4): 598-600 (1989)), permeability of in vitro skin equivalent cultures is much greater than that of intact human skin, i.e., the barrier function is defective in the culture systems Ponec, Int. J. Cosmetic Sci., 14: 245-264 (1992)). In an effort to improve the permeability barrier, a number of culture variables have been examined and some have led to improved properties of the cultures (Table 1). For example, growing the cultures at lowered relative humidity improves the barrier function of skin equivalent cultures (Mak et al., J. Invest. Dermatol., 96(3): 323-7 (1991)). It is believed that transepidermal water flux may serve as a regulatory signal for epidermal lipid synthesis and repair following disruption of the epidermal barrier (Grubauer et al., J. Lipid Res., 30(3): 323-33 (1989)). Hairless mice have also been used to demonstrate improved barrier function, epidermal morphology (SC thickness, number of lamellar membrane structures, number of lamellar bodies) and lipid content in response to lowered humidity.

A key biochemical difference between cultured skin substitutes and intact skin is the profile of extracellular lipids that are found in the outermost layer of normal skin. Cultures of differentiated keratinocytes are deficient in several ceramides that are major constituents of normal skin (Ponec et al., J. Invest. Dermatol., 109(3): 348-55 (1997)). Large quantities of these specialized extracellular lipids are secreted by differentiated keratinocytes and assembled into lipid bi-layers that are essential for normal epidermal barrier function. Comparison of the lipid composition between in vitro skin equivalent cultures and human skin revealed striking differences. Human skin contains seven forms of ceramides but the cultures produced primarily ceramides 1-3 and very little of ceramides 6 and 7. Re-establishing a more complete lipid profile has been the end-point of a number of studies. For example, addition of vitamin C to the media was found to be critical for a complete spectrum of ceramide lipids in skin equivalent cultures. Ceramides 6 and 7 contain hydroxylated sphingoid base and/or fatty acid, and production of these is likely facilitated by the presence of vitamin C. In this study, the lipid profiles of the commercially available skin equivalent cultures EPIDERM, SKINETHIC and Living Skin Equivalent were all deficient in ceramides 5, 6 and 7. Addition of vitamin C improved the lipid profile and the overall SC architecture as determined by electron microscopy.

TABLE 1

Effect of Substances added to in vitro Cultures on Barrier Function or Lipid Composition

| Compound | Barrier Function | Lipid Composition | Reference |
| --- | --- | --- | --- |
| EGF | | High triglycerides | Ponec et al., supra. |
| Estrogen | Accelerates | | Williams et al., J Investig. Dermatol. Symp. Proc., 3(2): 75-9 (1998). |
| FXAR activators | Accelerates | | Hanley et al., supra. |
| PPAR Activators | Accelerates | | Hanley et al. |
| Vitamin C | | Major improvement | Ponec et al. |
| Vitamin E | | No effect | Ponec et al. |
| Vitamin D | Improved/No effect | | Williams et al., Mac et al., supra. |

Activators of nuclear hormone receptors have been tested for their effects on barrier function development. Addition of vitamin D has led to improvements in some studies (Mak et al., supra) but not in others (Hanley et al., supra). Activators of the peroxisome proliferator-activated receptor (PPAR) and the farnesoid X-activated receptor (FXAR) accelerate barrier maturation in fetal rat skin in vitro and in utero. Structural changes were consistent with the reduction in transepidermal water loss, including the appearance of a distinct SC, a thickened stratum granulosum, and increased density of lamellar structures.

The aberrant lipid composition of skin equivalent cultures is also improved by grafting onto immunodeficient mice (Vicanova et al., J. Investig. Dermatol. Symp. Proc., 3(2): 114-20 (1998)). Cultured human keratinocytes retain the ability of generating a differentiated epidermis when grafted onto athymic mice. When cultured skin substitutes were examined between six months and two years after grafting, significant improvements in SC lipid composition and ultrastructure were observed. The high levels of triglycerides and low levels of cholesterol esters and free fatty acids observed in the in vitro cultures were normalized by six months after grafting. Ceramides 6 and 7, undetectable in the in vitro cultures, were expressed by the human cells after six months of grafting. These studies highlight the fact that current in vitro culture conditions are defective in their ability to produce skin equivalents with normal barrier function. Improved culture conditions that more closely mimic normal developmental signals should enhance barrier function development.

The development of barrier function in vivo is temporally regulated. In the rat, for example, at gestational day 19 fetal rat pups have no barrier, but by day 21 a competent barrier has formed (Aszterbaum et al., Pediatr. Res., 31(4 Pt 1): 308-17 (1992)). Development of a competent epidermal barrier occurs between embryonic day 15 and 16 of mouse gestation (Hardman et al., Development, 125: 1541-1552 (1998)). The functional barrier arises coincident with a multilayered SC and mature lamellar membranes in the SC. Expression of the corneocyte structural protein loricrin, filaggrin and involucrin increase during this period. Expression of enzymes involved in lipid processing, beta-glucocerebrosidase and steroid sulfatase, also increase. The process is also susceptible to manipulation by environmental and hormonal factors. PPAR and FXAR activators given for two days in utero accelerated the development of barrier function on day 19 pups as measured by reduction in transepidermal water loss. The treatments also improved SC morphology and gene expression of key structural proteins and enzymatic functions.

Accordingly, in some embodiments of the present invention, the following treatments, alone or in combination, are used to provide increased barrier function in organotypically cultured skin equivalents. In some embodiments, the organotypic cultures are supplemented with from about 1 micrograms/ml to about 200 micrograms/ml ascorbic acid, preferably about 50 micrograms/ml ascorbic acid. In other embodiments, the organotypic cultures are supplemented with about 1 to 200 μM linoleic acid, preferably about 30 μM linoleic acid. In still further embodiments, the organotypic cultures are supplemented with about 1 to 200 μM farnesol, preferably about 50 μM farnesol. In still other embodiments, the organotypic cultures are performed at from about 50 to 95% humidity, preferably about 75% humidity. Barrier function is conveniently evaluated in the skin equivalents by measuring surface electrical capacitance (SEC). In preferred embodiments, skin equivalents with improved barrier function as compared to control skin equivalents have a SEC value of less than about 5 times of the SEC observed in normal human skin (e.g., about 150-250 pF). In particularly preferred embodiments, skin equivalents with improved barrier function as compared to control skin equivalents have an SEC of less than about 2-3 times of the SEC observed in normal human skin (e.g., about 80-120 pF). In other embodiments, the skin equivalents with improved barrier function are characterized by ceramide content. Accordingly, in some embodiments, the content of ceramides 5-7 is between about 20-50% of the total ceramide mass, preferably about 30-45% of the total ceramide mass. In other embodiments, the content of ceramide 2 is between about 10 to 40% of the total ceramide mass, preferably about 20 to 30% of total ceramide content.

The present invention further provides additional methods and compositions for producing skin equivalents with improved characteristics, including improved barrier function. The improved methods and compositions are described in the following sections: 1) Culture Techniques and 2) Culture Media.

1. Culture Techniques

The present invention provides improved organotypic culture techniques for producing skin equivalents with superior properties. In some embodiments, a dermal equivalent is prepared. In preferred embodiments, the dermal equivalent comprises collagen and human fibroblasts. The present invention is not limited to the use of any particular type of collagen. Indeed, the use of a variety of types of collagen is contemplated, including, but not limited to rat tail tendon collagen (Type I). Likewise, the present invention is not limited to any particular type of fibroblasts. Indeed, the use of a variety of different types of fibroblasts is contemplated including, but not limited to, NHDF (Normal Human Dermal Fibroblasts) cells and cells harvested from a donor or patient.

The present invention also is not limited to the use of any particular concentration or amount of collagen. In preferred embodiments, the dermal equivalents are prepared with about 0.2 mg collagen per square centimeter of said dermal equivalent to 2.0 mg collagen per square centimeter of said dermal equivalent. In more preferred embodiments, the dermal equivalent contains about 0.22 mg collagen per square centimeter of said dermal equivalent to 1.0 mg collagen per square centimeter of said dermal equivalent. In most preferred embodiments, the dermal equivalent contains about 0.5 mg collagen per square centimeter of said dermal equivalent.

In contrast to most previously described methods for organotypic skin culture, a mixture of collagen and fibroblasts is applied directly to whatever culture device is being used. The applicants have discovered that the presence of an acelluar first layer is not necessary to obtain good contraction and adherence to the culture device. In some embodiments, the fibroblasts are included in a final concentration of from about 10,000 cells/ml to about 100,000 cells/ml, preferably about 50,000 cells/ml.

Figure 4:
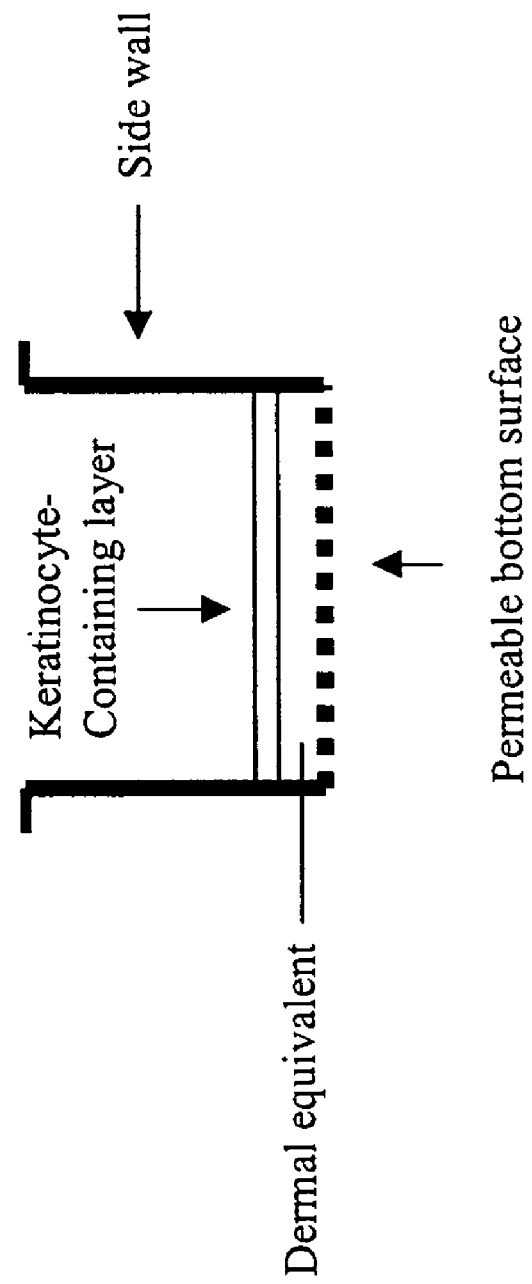
FIG. 4 provides a depiction of the culture wells of some embodiments of the present invention.

A variety of culture devices find use in the present invention. Preferred culture devices (see FIG. 4) are growth chambers comprised of a side-wall and a bottom surface. In some preferred embodiments, the growth chamber is generally cup-shaped. In preferred embodiments, the bottom surface is permeable to the culture medium. A non-limiting example of a suitable permeable surface material is porous polycarbonate. The present invention is compatible with commercially available culture devices including MILLICELL (MILLIPORE) and TRANSWELL (CORNING) culture inserts. The MILLICELL inserts are especially useful for the preparation of skin equivalents used for testing purposes (e.g., skin equivalents of about 1 cm in diameter). The inventors have discovered that a plurality of MILLICELL-size inserts may be incubated in a larger petri dish (i.e., a 100 mm culture dish). The TRANSWELL inserts are useful for the production of larger skin equivalents (e.g., about 10 cm in diameter). These larger skin equivalents can be used as grafts, for larger scale testing, or dissected into smaller testing formats.

In preferred embodiments, the freshly poured dermal equivalents are submerged in culture media and cultured until contraction of the dermal equivalent occurs. This creates a dermal equivalent with a generally concave appearance. In previously described methods, after contraction of the dermal layer, the dermal layer is seeded with keratinocytes and then resubmerged. The organotypic culture is then lifted to the air interface of the culture medium after about 4-7 days. In contrast to these previously described methods, the present inventors have found that is preferable to lift the dermal equivalent to the air interface prior to seeding with keratinocytes. The culture is then preferably maintained at the air interface as stratification occurs. Accordingly, in some embodiments, the dermal equivalent is preferably lifted to the air interface and maintained for greater than about 6 hours prior to seeding. In more preferred embodiments, the dermal equivalent is preferably lifted to the air interface and maintained for greater than about twelve hours prior to seeding. In most preferred embodiments, the dermal equivalent is preferably lifted to the air interface and maintained for greater than about twenty-four hours prior to seeding. In some embodiments, the dermal equivalent is maintained for more than 24 hours at the air interface to provide a pre-made dermal equivalent for later use.

The culture techniques of the present invention provide skin equivalents with superior properties. In preferred embodiments, the skin equivalents have improved barrier function as compared to previously described skin equivalents. In still further preferred embodiments, the present invention provides dermal equivalents for use in producing skin equivalents with superior properties. In some embodiments, the dermal equivalents are characterized by containing increased concentrations of collagen as described above.

In still further preferred embodiments, the present invention provides compositions for use in producing skin equivalents. In some embodiments, the compositions comprise a growth chamber having a bottom surface and a side-wall. In further embodiments, the growth chamber includes a dermal equivalent adjacent to the bottom surface. In still further embodiments, the dermal equivalent is substantially adhered to the side-wall.

The inventors have also discovered that the seeding density of the keratinocytes on the dermal equivalents can affect the quality of the resulting skin equivalent. Accordingly, in some embodiments of the present invention, the seeding density is increased by approximately an order of magnitude over previously described methods. In some embodiments, the seeding density of keratinocytes ranges from about $1 \times 10^5$ to $1 \times 10^6$ cells/cm$^2$ of dermal equivalent. In still further preferred embodiments, the seeding density of keratinocytes is about $4.65 \times 10^5$ cells/cm$^2$ of dermal equivalent.

Barrier function is conveniently evaluated in the skin equivalents by measuring surface electrical capacitance (SEC). In preferred embodiments, skin equivalents with improved barrier function as compared to control skin equivalents have a SEC value of less than about 5 times of the SEC observed in normal human skin (e.g., about 150-250 pF). In particularly preferred embodiments, skin equivalents with improved barrier function as compared to control skin equivalents have an SEC of less than about 2-3 times of the SEC observed in normal human skin (e.g., about 80-120 pF). In other embodiments, the skin equivalents with improved barrier function are characterized by ceramide content. Accordingly, in some embodiments, the content of ceramides 5-7 is between about 20-50% of the total ceramide mass, preferably about 30-45% of the total ceramide mass. In other embodiments, the content of ceramide 2 is between about 10 to 40% of the total ceramide mass, preferably about 20 to 30% of total ceramide content.

2. Culture Media

The present invention provides improved organotypic culture media for producing skin equivalents with superior properties. In some embodiments, the culture media of the present invention are Ham's F12 medium and Dulbecco's modified Eagle's medium (DMEM). In some embodiments, the Ham's F12 and DMEM are supplemented with at least one of the following supplements: bovine serum albumin, isoproterenol, carnitine, serine, oleic acid, linoleic acid, arachidonic acid, α-tocopherol, ascorbic acid, and epidermal growth factor (EGF). In other embodiments, at least one of bovine serum albumin, isoproterenol, carnitine, serine, oleic acid, linoleic acid, arachidonic acid, α-tocopherol, ascorbic acid, and EGF is (are) provided in concentration(s) sufficient to improve barrier function in in vitro cultured skin equivalents. In still other embodiments, the medium comprises a serum supplement, preferably Fetal Clone II. In some embodiments, the medium further comprises at least one of the following supplements: hydrocortisone, cholera toxin, insulin, adenine, and CaCl$_2$. In preferred embodiments, the bovine serum albumin is provided at a concentration of about 0.1 mg/ml to 20 mg/ml, preferably about 1 mg/ml, the isoproterenol is provided at a concentration of about 0.1-10.0 μM, the carnitine is provided at a concentration of about 1.0-100.0 µM, the serine is provided at a concentration of about 1.0-100.0 µM, the oleic acid is provided at a concentration of about 1.0-100.0 µM, the linoleic acid is provided at a concentration of about 1.0-100.0 µM, the arachidonic acid is provided at a concentration of about 10.0-100.0 µM, the α-tocopherol is provided at a concentration of about 0.1-10.0 µM, the ascorbic acid is provided at a concentration of about 0.005-5.0 mg/ml, and the epidermal growth factor is provided at a concentration of about 0.1-10.0 ng/ml.

C. Genetic Modification of Cells for Improved Barrier Function

The present invention also contemplates that barrier function can be improved by expressing heterologous GKLF in the cells described in Section A. Expression of heterologous GKLF may also be combined with the improved culture conditions described in Section B. The final stages of epidermal differentiation are preceded by increased expression of numerous genes that encode the enzymes required for the biochemical modifications that result in the stratum corneum. In addition, culture conditions that stimulate keratinocyte differentiation or experimental disruption of the skin barrier function result in increased expression of enzymes involved in extracellular lipid synthesis and metabolism. These gene expression changes indicate that one or more regulatory transcription factors are responsible for altering the gene expression profile of differentiating keratinocytes to facilitate development of the epidermal barrier. The precise timing of skin barrier function in development suggests a precise temporal control by a developmental switch. Complex developmental programs can be initiated by the action of one or a small number of key regulatory transcription factors, sometimes called master regulators or selector genes. A recent study on a knock-out mutation in the transcription factor Kruppel-like factor 4 (Klf4) may have identified one of the key regulators of barrier function in the skin (Segre et al., Nat. Genet., 22(4): 356-60 (1999)).

Klf4 mutant mice are born in normal numbers but die shortly (<15 hrs) after birth apparently from hypo-volemic shock as a result of excessive evaporative fluid loss. Further analysis demonstrated that, while normal mice develop an intact epidermal barrier function by day 17.5 of gestation, Klf4 mutant mice fail to develop this barrier function and have an epidermis that exhibits excessive trans-epidermal water loss. Klf4 is expressed in the differentiating layers of the epidermis, the upper spinous and granular layers. In contrast to the defects caused in other mutant mouse lines, the absence of Klf4 does not result in gross alterations of the epidermal ultrastructure or in lipid profiles. This led to the hypothesis that its primary role is in the acquisition of barrier function. Consistent with this, defects were observed in the stratum granulosum in the keratohyalin granules and flattening of SC cells. By EM, the intercellular lamellae were discontinuous in the mutant skin. The defect in Klf-4 mutant skin was not rescued by grafting it onto foster mice. Klf4 is a member of a family of transcription factors; other members are implicated in tissue-specific differentiation events in erythroid cells and T-cells. Analysis of gene expression differences between wild-type and Klf4 mutant mice led to the identification of three genes that were up-regulated in the mutant skin, suggesting that Klf4 may repress the expression of these genes normally. The observation that loss of Klf4 has no other observable effects on mouse development suggests that Klf4 functions primarily to regulate the development of the epidermal permeability barrier. The role of Klf4 in the acquisition of epidermal barrier function raises the possibility that expression of Klf4 in cultured skin substitutes might improve the barrier properties of these synthetic skin cultures.

Accordingly, in some embodiments, primary keratinocytes or immortalized keratinocytes are transfected with a vector encoding a functional GKLF homolog. It is contemplated that when these keratinocytes are organotypically cultured, the resulting skin equivalent will exhibit improved barrier function as compared to organotypic cultures formed from non-transfected, control keratinocytes. In preferred embodiments, skin equivalents with improved barrier function as compared to control skin equivalents have a SEC value of less than about 5 times of the SEC observed in normal human skin (e.g., about 150-250 pF). In particularly preferred embodiments, skin equivalents with improved barrier function as compared to control skin equivalents have an SEC of less than about 2-3 times of the SEC observed in normal human skin (e.g., about 80-120 pF). In other embodiments, the skin equivalents with improved barrier function are characterized by ceramide content. Accordingly, in some embodiments, the content of ceramides 5-7 is between about 20-50% of the total ceramide mass, preferably about 30-45% of the total ceramide mass. In other embodiments, the content of ceramide 2 is between about 10 to 40% of the total ceramide mass, preferably about 20 to 30% of total ceramide content.

The present invention is not limited to the use of any particular homolog or variant of GKLF. Indeed, a variety of GKLF variants may be used so long as they retain at least some of the activity of wild-type GKLF. In particular, it contemplated that both mouse (SEQ ID NO:1) and human (SEQ ID NO:2) GKLF find use in the present invention. Additionally, it is contemplated that GKLF variants encoded by sequences that hybridize to SEQ ID NOs: 1 and 2 under conditions of from low to high stringency will find use in the present invention. Functional variants can be screened for by expressing the variant in an appropriate vector (described in more detail below) in keratinocytes, using the heratinocytes to produce a skin equivalent, and analyzing the skin equivalent for increased barrier function. Alternatively, functional variants can be identified by an electrophoretic mobility shift assay as described in (Zhang et al., J. Biol. Chem., 273(28): 17917-25 (1998).

In some embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., GKLF function) for such purposes as increasing binding affinity of GKLF for its nucleic acid ligand. Such modified peptides are considered functional equivalents of peptides having an activity of GKLF as defined herein. A modified peptide can be produced in which the nucleotide sequence encoding the polypeptide has been altered, such as by substitution, deletion, or addition. In particularly preferred embodiments, these modifications do not significantly reduce the activity of the modified GKLF. In other words, construct "X" can be evaluated in order to determine whether it is a member of the genus of modified or variant GKLF's of the present invention as defined functionally, rather than structurally. In preferred embodiments, the activity of variant or mutant GKLF is evaluated by the methods described above.

Moreover, as described above, variant forms of GKLF are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of GKLF disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

The heterolgous GKLF is expressed in keratinocytes by using a suitable vector and regulatory sequences. In some preferred embodiments, either a involucrin or transglutaminase 3 promoters are utilized. In other preferred embodiments, the expression of GKLF will be driven by the inducible promoter system of the pTetOn plasmid (Clontech, Palo Alto, Calif.). It is contemplated that a number of other mammalian expression vectors are suitable for use in the present invention, including, but not limited to, pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements. Additionally, the Klf 4 gene may be inserted via a retroviral vector. In particularly preferred embodiments, the retroviral vector is pseudotyped retroviral vector (Clontech, Palo Alto, Calif.). Transfection can be accomplished by any method known in the art, including but not limited to calcium-phosphate coprecipitation, electroporation, microparticle bombardment, liposome mediated transfection, or retroviral infection.

D. Uses of Skin Substitutes Having Improved Barrier Function

It is contemplated that the skin substitutes of the present invention have a variety of uses. These uses include, but are not limited to, use for screening compounds (e.g., irritants), substrates for culturing tumors and pathological agents (e.g., human papilloma virus), and use for wound closure and burn treatment. These uses are described in more detail below.

1. Use for Screening Compounds

The skin equivalents of the present invention may be used for a variety of in vitro tests. In particular, the skin equivalents find use in the evaluation of: skin care products, drug metabolism, cellular responses to test compounds, wound healing, phototoxicity, dermal irritation, dermal inflammation, skin corrosivity, and cell damage. The skin equivalents are provided in a variety of formats for testing, including but not limited to, 6-well, 24-well, and 96-well plates. Additionally, the skin equivalents can be divided by standard dissection techniques and then tested. The skin equivalents of the present invention have both an epidermal layer with a differentiated stratum corneum and dermal layer that includes dermal fibroblasts. As described above, in particularly preferred embodiments, the epidermal layer is derived from immortalized NIKS cells. Other preferred cell lines, including NIKS cells, are characterized by i) being immortalized; ii) being nontumorigenic; iii) forming cornified envelopes when induced to differentiate; iv) undergoing normal squamous differentiation in organotypic culture; and v) maintaining cell type-specific growth requirements in submerged culture, wherein said cell type-specific growth requirements include 1) exhibition of morphological characteristics of normal human keratinocytes when cultured in standard keratinocyte growth medium in the presence of mitomycin C-treated 3T3 feeder cells; 2) dependence on epidermal growth factor for serial cultivation; and 3) inhibition of growth by transforming growth factor $\beta 1$.

The present invention encompasses a variety of screening assays. In some embodiments, the screening method comprises providing a skin equivalent of the present invention and at least one test compound or product (e.g., a skin care product such as a moisturizer, cosmetic, dye, or fragrance; the products can be in any from, including, but not limited to, creams, lotions, liquids and sprays), applying the product or test compound to skin equivalent, and assaying the effect of the product or test compound on the skin equivalent. A wide variety of assays are used to determine the effect of the product or test compound on the skin equivalent. These assays include, but are not limited to, MTT cytotoxicity assays (Gay, The Living Skin Equivalent as an In Vitro Model for Ranking the Toxic Potential of Dermal Irritants, Toxic. In Vitro (1992)) and ELISA to assay the release of inflammatory modulators (e.g., prostaglandin E2, prostacyclin, and interleukin-1-alpha) and chemoattractants. The assays can be further directed to the toxicity, potency, or efficacy of the compound or product. Additionally, the effect of the compound or product on growth, barrier function, or tissue strength can be tested.

In particular, the present invention contemplates the use of the skin equivalents for high throughput screening of compounds from combinatorial libraries (e.g., libraries containing greater than $10^4$ compounds). In some embodiments, the cells are used in second messenger assays that monitor signal transduction following activation of cell-surface receptors. In other embodiments, the cells can be used in reporter gene assays that monitor cellular responses at the transcription/ translation level. In still further embodiments, the cells can be used in cell proliferation assays to monitor the overall growth/ no growth response of cells to external stimuli.

In second messenger assays, the skin equivalents are treated with a compound or plurality of compounds (e.g., from a combinatorial library) and assayed for the presence or absence of a second messenger response. In some preferred embodiments, the cells (e.g., NIKS cells) used to create the skin equivalents are transfected with an expression vector encoding a recombinant cell surface receptor, ion-channel, voltage gated channel or some other protein of interest involved in a signaling cascade. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels) (Denyer et al., Drug Discov. Today 3:323-32 (1998); Gonzales et al., Drug. Discov. Today 4:431-39 (1999)). Examples of reporter molecules include, but are not limited to, florescence resonance energy transfer systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the cells comprising the skin equivalents are loaded with the indicator prior to exposure to the compound. Responses of the host cells to treatment with the compounds can be detected by methods known in the art, including, but not limited to, fluorescence microscopy, confocal microscopy, flow cytometry, microfluidic devices, FLIPR systems (Schroeder and Neagle, J. Biomol. Screening 1:75-80 (1996)), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The skin equivalents of the present invention are also useful in reporter gene assays. Reporter gene assays involve the use of host cells transfected with vectors encoding a nucleic acid comprising transcriptional control elements of a target gene (i.e., a gene that controls the biological expression and function of a disease target or inflammatory response) spliced to a coding sequence for a reporter gene. Therefore, activation of the target gene results in activation of the reporter gene product. This serves as indicator of response such an inflammatory response. Therefore, in some embodiments, the reporter gene construct comprises the 5' regulatory region (e.g., promoters and/or enhancers) of a gene that is induced due to skin inflammation or irritation or protein that is involved in the synthesis of compounds produced in response to inflammation or irritation (e.g., prostaglandin or prostacyclin) operably linked to a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green, red, yellow, or blue fluorescent protein, is detected through the use of chemiluminescent, colorimetric, or bioluminecent products of specific substrates (e.g., X-gal and luciferin). Comparisons between compounds of known and unknown activities may be conducted as described above.

In other preferred embodiments, the skin equivalents find use for screening the efficacy of drug introduction across the skin or the affect of drugs directed to the skin. In these embodiments, the skin equivalents are treated with the drug delivery system or drug, and the permeation, penetration, or retention or the drug into the skin equivalent is assayed. Methods for assaying drug permeation are provided in Asbill et al., Pharm Res. 17(9): 1092-97 (2000). In some embodiments, the skin equivalents are mounted on top of modified Franz diffusion cells. The skin equivalents are allowed to hydrate for one hour and then pretreated for one hour with propylene glycol. A saturated suspension of the model drug in propylene glycol is then added to the skin equivalent. The skin equivalent can then be sampled at predetermined intervals. The skin equivalents are then analyzed by HPLC to determine the concentration of the drug in the sample. Log P values for the drugs can be determined using the ACD program (Advanced Chemistry Inc., Ontario, Canada). These methods may be adapted to study the delivery of drugs via transdermal patches or other delivery modes.

In still further preferred embodiments, the seeded dermal equivalents, which have not yet undergone differentiation, find use in assays for compounds that inhibit, accelerate, or otherwise effect differentiation of the seeded keratinocytes.

2. Skin Irritancy Testing

In some embodiments, the skin equivalents of the present invention are utilized in reporter gene assays for the testing of compounds for their skin irritant activity. In other embodiments, the present invention provides methods of utilizing the skin equivalent for identifying novel genes that are responsive to known skin irritants. The novel genes identified using the methods of the present invention further find use in the generation of additional reporter gene constructs for screening potential skin irritants.

Initial screening experiments have been carried out to confirm that stable transfectants of NIKS keratinocytes expressing a transgene (GFP) exhibit normal stratification in organotypic culture. NIKS cells have been stably transfected with the *Aequorea Victoria* green fluorescent protein (GFP) and a clonal population has been isolated. The ability of these stably transfected GFP-positive NIKS cells (NIKS$^{GFP}$) to recreate normal tissue architecture in organotypic cultures was tested. Samples were frozen, cryostat sectioned, and analyzed by fluorescent microscopy. Cultures were first examined for expression and localization of GFP. In addition, sections were stained with Hoechst, a nuclear dye, and hematoxylin and eosin (H&E) to orient and visualize the cellular layers of the cultures. Sections of organotypic cultures were visualized using an IX-70 inverted fluorescent microscope (Olympus) equipped with GFP and Hoechst filters (Magnification, 400×). Sections of NIKS$^{GFP}$ cultures showed that GFP was present throughout all layers of the organotypic culture with the most intense fluorescence observed in the cornified layer.

The histology of the organotypic NIKS$^{GFP}$ cultures was next compared with those of untransfected NIKS cells and parental BC-1-Ep keratinocytes. H&E-stained sections of NIKS$^{GFP}$ rafts showed a well organized, defined basal layer and excellent stratification with no abnormalities relative to untransfected controls and the parental BC-1-Ep keratinocytes. All three cultures show comparable cell stratification with no noticeable histological differences at the light microscope level.

To further examine the ability of NIKS$^{GFP}$ cells to differentiate normally, the expression of several keratinocyte-specific differentiation markers was analyzed by immunofluoresence microscopy. As keratinocytes move to a suprabasal position within the tissue, they synthesize differentiation-specific proteins. Keratinocytes cease production of the basal keratins KS and K14 and begin expressing the differentiation specific K1 and K10 keratins, which are expressed throughout the rest of the layers in the epidermis. Sections of the organotypic cultures were examined for expression and localization of K10 using indirect immunofluorescence. Keratin 10 was expressed normally in the suprabasal layers in BC-1-Ep, NIKS, and NIKS$^{GFP}$ organotypic cultures. To further characterize the differentiation pattern of the NIKS$^{GFP}$ cells, the expression and localization of filaggrin, which is a late-stage differentiation marker, was examined. Keratinocyte differentiation into the stratum granulosum is distinguished by the presence of distinct keratohyalin granules. These granules are composed of filaggrin and other proteins that are precursors for the production of the cornified envelope. Filaggrin staining in sections of all organotypic cultures displayed a punctate pattern characteristic of cells in the granular layer.

In addition, the expression and localization of the adherens junctional components, E- and P-cadherin, was analyzed. In normal epidermis two members of the classical cadherin family, E- and P-cadherin are expressed, both of which play an important role in differentiation and cell adhesion in the epidermis. P-cadherin expression is limited to the basal layer and E-cadherin is located throughout the epidermis. The E-cadherin staining pattern is normal and localized to the cell-cell borders in sections of all three cultures. These data demonstrate that genetically-modified NIKS cells exhibit normal differentiation. Thus, it is contemplated that NIKS cells containing reporter gene constructs will form cultured skin equivalents similar to those formed with primary keratinocytes.

Experiments were also performed to confirm that in response to known irritants, NIKS cells secrete a cytokine known to be secreted in response to skin irritants. Example 3 demonstrated that NIKS cells secrete IL-1α in response to a known skin irritant.

i) Reporter Gene Assays

In some embodiments, the present invention provides skin equivalent (e.g., NIKS) cells comprising a reporter gene construct responsive to skin irritants. Suitable reporter gene constructs include, but are not limited to, those described above. In some embodiments, the cells further have improved barrier function.

Previous studies indicated that IL-8 expression correlates well with skin irritation (de Brugerolle de Fraissinette et al., Cell Biology and Toxicology, 15:121 [1999]). Published sequences from the IL-8 gene include 1,482 bp of DNA upstream from the transcription start site and 102 bp of transcribed, untranslated DNA upstream from the IL-8 coding region (Mukaida et al., J. Immunology, 143:1366 [1989]). Chang and collaborators have found that a reporter gene containing IL-8 promoter sequences between −1472 and +19 is induced by trans-retinoic acid in tracheobronchial epithelial cells (Chang et al., Am J. Respir Cell Mol. Biol. 22:502 [2000]). Abe et al. have shown that IL-8 promoter fragments containing as little as 130 bp upstream from the transcription start site direct inducible expression of a luciferase reporter gene (Abe et al., Am J. Respir Cell Mol. Biol., 22:51 [2000]). This fragment contains binding sites for NF-κB, AP-1, and NF-IL-6 and the binding sites for these factors are required for inducible IL-8 expression (reviewed in Roebuck, J. Interferon Cytokine Res., 19:429 [1999]).

Accordingly, in some embodiments, the present invention provides skin equivalent (e.g., NIKS) cells comprising a reporter gene in which expression of a reporter gene (e.g., an enzyme) is controlled by the regulatory region of an irritant responsive gene. The present invention is not limited to any irritant responsive promoter. Indeed, a variety of promoters are contemplated, including but not limited to IL-8 and IL-1α. The present invention is not limited to the entire regulatory region of the irritant responsive gene. Indeed, in some embodiments, fragments comprising a portion of the regulatory region are contemplated. Any region or regions that are responsive to an irritant find use in the present invention. Guidance for determining if a given region of a gene is responsive is provided in Example 4 below.

The present invention is not limited to any particular reporter gene. Indeed, a variety of reporter genes are contemplated, including but not limited to, secreted alkaline phosphatase (SEAP), chloramphenicol transferase, firefly and bacterial luciferases, -galactosidase, -lactamase, and green fluorescent protein. The production of these proteins, with the exception of green fluorescent protein, is detected through the use of chemiluminescent, colorimetric, or bioluminecent products of specific substrates (e.g., X-gal and luciferin).

Reporter gene contructs contained on a plasmid are generated using standard molecular biology techniques. For example, in some embodiments, pSEAP (Tropix, Bedford, Mass.) is used to generate a reporter gene construct. pSEAP is a mammalian expression vector lacking a promoter and containing the SEAP gene (Berger et al., 1988). The vector contains a polylinker for promoter/enhancer insertion, as well as an intron and polyadenylation signals from SV40. The vector can be propagated in E. coli due to the pUC19 derived origin of replication and ampicillin resistance gene. Other suitable vectors for the generation of reporter gene constructs are available (e.g., including but not limited to, pβ-Gal (β-galactosidase reporter); Tropix).

Stable skin equivalent (e.g., NIKS) cell lines are established which contain the reporter gene, and these transfected cells are used to generate in vitro skin equivalents. The cells are then used to monitor expression of the reporter gene construct in response to a panel of irritant compounds (See Example 4).

Expression by the reporter gene may be measured using any suitable assay. In some preferred embodiments, the present invention utilizes gene expression read-outs of skin irritants by NIKS-derived cell lines harboring reporter gene constructs. The use of such assays increases the speed and lowers the costs of using the assays for testing new compounds. For Example, in some embodiments, chemiluminescent reporter gene assays that can be performed in 30 minutes or less are utilized. Example 4 describes one illustrative assay that finds use in the present invention.

ii) Screening for Novel Irritant Responsive Genes

In other embodiments, the present invention provides methods and compositions for identifying novel irritant responsive genes. In some embodiments, in order to obtain data that correlates well with irritant exposure in the general population, global gene expression changes in organotypic cultures of primary human keratinocytes from pooled donors that have been exposed to known skin irritants are assayed.

Novel genes identified by the methods of the present invention find use in irritancy testing assays using skin equivalent (e.g., NIKS) derived gene reporter cell lines and an irritancy-predictor gene expression array.

Gene expression arrays have been used successfully to gain new insights into the global gene expression responses of mammalian cells to serum (Iyer et al., Science 283:83 [1999]) and specific growth factor signaling pathways (Fambrough et al., Cell 97:727 [1999]). In addition, it has recently been established that cluster analysis (Eisen et al., PNAS 95:14863 [1998] of gene expression patterns can distinguish and predict different forms of cancer (acute myeloid leukemia versus acute lymphoblastic leukemia) (Golub et al., Science 286:531 [1999]). Analysis of the expression of 6817 human genes in these two forms of cancer led to the generation of a "predictor" array of the 50 most informative genes that successfully distinguished an independent set of patient samples (Golub et al., Supra). This is a powerful example of DNA array analysis to derive a subset of known and novel genes whose overall pattern can distinguish the subtleties of two different cellular states of disease. Accordingly, in some embodiments, the present invention uses gene arrays to identify novel genes secreted in response to known irritants.

The present invention is not limited to any one gene expression array. Gene expression arrays are available in a variety of formats from a number of commercial sources, including but not limited to, filter-based arrays (Research Genetics and Clontech), glass-slide cDNA arrays (Incyte-Genome Systems) and oligonucleotide DNA microarrays (Affymetrix). In one illustrative example (Example 5), cDNA microarrays (Genome Systems) are used to screen cultured human keratinocytes treated with known irritants.

The screening methods of the present invention are used to generate a database of gene expression changes in human keratinocytes in response to multiple known skin irritants. The information contained in the database finds use in the development of irritancy-predictor gene expression arrays. Such arrays are utilized to generate an irritancy profile that is likely to be a better predictor of in vivo skin irritation than single endpoint assays currently in use. Simple gene expression read-outs of skin irritants by skin equivalent (e.g., NIKS) derived cell lines harboring reporter gene constructs will increase the speed and lower the costs of using these assays for testing new compounds.

3. Substrates for Culturing Tumors and Pathological Agents

It is contemplated that skin equivalents of the present invention are also useful for the culture and study of tumors that occur naturally in the skin as well as for the culture and study of pathogens that affect the skin. Accordingly, in some embodiments, it is contemplated that the skin equivalents of the present invention are seeded with malignant cells. By way of non-limiting example, the skin equivalents can be seeded with malignant SCC13y cells as described in U.S. Pat. No. 5,989,837, which is incorporated herein by reference, to provide a model of human squamous cell carcinoma. These seeded skin equivalents can then be used to screen compounds or other treatment strategies (e.g., radiation or tomotherapy) for efficacy against the tumor in its natural environment. Thus, some embodiments of the present invention provide methods comprising providing a skin equivalent comprising malignant cells or a tumor and at least one test compound, treating the skin equivalent with the compound, and assaying the effect of the treatment on the malignant cells or tumors. In other embodiments of the present invention, methods are provided that comprise providing a skin equivalent comprising malignant cells or a tumor and at least one test therapy (e.g., radiation or phototherapy) treating the skin equivalent with the therapy, and assaying the effect of the therapy on the malignant cells or tumors.

In other embodiments, the skin equivalents are used to culture and study skin pathogens. By way of non-limiting example, the skin equivalents are infected with human papilloma virus (HPV) such as HPV18. Methods for preparing skin equivalents infected with HPV are described in U.S. Pat. No. 5,994,115, which is incorporated herein by reference. Thus, some embodiments of the present invention provide methods comprising providing a skin equivalent infected with a pathogen of interest and at least one test compound or treatment and treating the skin equivalent with the test compound or treatment. In some preferred embodiments, the methods further comprise assaying the effect the test compound or treatment on the pathogen. Such assays may be conducted by assaying the presence, absence, or quantity of the pathogen in the skin substitute following treatment. For example, an ELISA may be performed to detect or quantify the pathogen. In some particularly preferred embodiments, the pathogen is viral pathogen such as HPV.

4. Wound Closure and Burn Treatment

The skin equivalents of the present invention find use in wound closure and burn treatment applications. The use of autografts and allografts for the treatment of burns and wound closure is described in Myers et al., A. J. Surg. 170(1):75-83 (1995) and U.S. Pat. Nos. 5,693,332; 5,658,331; and 6,039,760, each of which is incorporated herein by reference. In some embodiments, the skin equivalents may be used in conjunction with dermal replacements such as DERMAGRAFT. In other embodiments, the skin equivalents are produced using both a standard source of keratinocytes (e.g., NIKS cells) and keratinocytes from the patient that will receive the graft. Therefore, the skin equivalent contains keratinocytes from two different sources. In still further embodiments, the skin equivalent contains keratinocytes from a human tissue isolate. Accordingly, the present invention provides methods for wound closure, including wounds caused by burns, comprising providing a skin equivalent having improved barrier function according to the present invention and a patient suffering from a wound and treating the patient with the skin equivalent under conditions such that the wound is closed.

5. Gene Therapy

In still further embodiments, the skin equivalent is engineered to provide a therapeutic agent to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, and antisense RNA. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathesis) in which the graft serves as wild-type tissue. It is contemplated that delivery of the therapeutic agent corrects the defect. In some embodiments, the keratinocytes used to form the skin equivalent are transfected with a DNA construct encoding a therapeutic agent (e.g., insulin, clotting factor IX, erythropoietin, etc) and the skin equivalent is grafted onto the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue specific, and keratinocyte specific promoters. In some embodiments, the nucleic acid encoding the therapeutic agent is introduced directly into the keratinocytes (i.e., by calcium phosphate co-precipitation or via liposome transfection). In other preferred embodiments, the nucleic acid encoding the therapeutic agent is provided as a vector and the vector is introduced into the keratinocytes by methods known in the art. In some embodiments, the vector is an episomal vector such as a plasmid. In other embodiments, the vector integrates into the genome of the keratinocytes. Examples of integrating vectors include, but are not limited to, retroviral vectors, adeno-associated virus vectors, and transposon vectors.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin).

EXAMPLE 1

Effect of Culture Conditions on Epidermal Barrier Function of NIKS Cells

While a number of culture conditions have been shown to enhance various aspects of barrier function (see Table 1, supra), there has been no systematic attempt to examine synergistic effects of these conditions. This example provides an assessment of the combined effects of ascorbic acid, PPAR activators (linoleic acid), FXAR activators (farnesol), and reduced relative humidity on epidermal barrier function of NIKS organotypic cultures. Barrier properties of treated cultures are evaluated by measuring surface electrical capacitance (SEC) (Boyce et al., J. Invest. Dermatol., 107(1): p. 82-7 (1996)), analysis of extracellular lipid composition, and by ultrastructural examination of tissue sections by electron microscopy.

The culture conditions to be evaluated are presented in Table 2. Culture supplements are added individually or in combination to the cornification medium at the indicated concentrations. The organotypic cultures are incubated at the air/liquid interface for 14-17 days before analysis. The NIKS-based cultures consist of dermal and epidermal compartments. The dermal compartment consists of a collagen base and is formed by mixing normal human neonatal fibroblasts, strain CI-1-F, with Type I collagen in Ham's F-12 medium containing 10% fetal calf serum (FCS) and penicillin/streptomycin (P/S) and allowing contraction. The epidermal compartment is produced by seeding the NIKS cells on the contracted collagen gel in 25 µl of a mixture of Ham's F-12:DME, (3:1, final calcium concentration 1.88 mM) supplemented with 0.2% FCS, 0.4 µg/ml hydrocortisone (HC), 8.4 ng/ml cholera toxin (CT), 5 µg/ml insulin (Ins), 24 µg/ml adenine (Ade), and 100 units/ml P/S. Cells are allowed to attach 2 hours before flooding culture chamber with media (day 0). On days 1 and 2 cells are refed. On day 4, cells are lifted to the air interface with a cotton pad and switched to cornification medium containing Ham's F-12:DME, (3:1, final calcium concentration 1.88 mM) supplemented with 2% FCS, 0.4 µg/ml HC, 8.4 ng/ml CT, 5 µg/ml Ins, 24 µg/ml Ade, and P/S. Cells are fed fresh cornification medium every 3 days.

For measurement of SEC, the impedence of the culture surfaces is determined using a Dermaphase 9003 impedence meter (NOVA Technologies Corp, Portsmouth, N.H.). This instrument provides a measure of the electrical conductivity of the skin surface, which is directly related to the sample's hydration state and barrier properties. The probe is placed in contact with the culture surface and readings are taken immediately upon probe contact and at the end of the 10 second period. The initial reading is then compared to the reading after the probe has been in place for 10 seconds. An increase in the reading after 10 seconds reflects increased hydration of the culture surface due to occlusion of the skin surface by the probe. Since surface hydration is largely determined by the permeability of the stratum corneum, the magnitude of the difference between the initial and final SEC readings provides a measure of the barrier properties of the cultures. Each culture condition is analyzed in triplicate and the average impedence measurements compared to standard, unsupplemented culture conditions to assess improvements in barrier function. SEC readings from in vitro cultures are also compared to SEC measurements obtained from normal human skin. Previous studies have shown that the SEC values of in vitro skin substitutes (400 pF) are about ten-fold higher than those observed with normal human skin. The goal of these experiments is to develop conditions that improve barrier function of organotypic keratinocyte cultures such that SEC readings of these cultures are at most 2-3 fold higher than normal skin.

TABLE 2

Culture Supplements and Humidity

| Ascorbic acid | Linoleic Acid | Farnesol | Humidity |
| --- | --- | --- | --- |
| | | | 100% |
| | | | 75% |
| 50 micrograms/ml | | | 100% |
| 50 micrograms/ml | | | 75% |
| | 30 micromolar | | 100% |
| | 30 micromolar | | 75% |
| | | 50 micromolar | 100 |
| | | 50 micromolar | 75% |
| 50 micrograms/ml | 30 micromolar | | 100% |
| 50 micrograms/ml | 30 micromolar | | 75% |
| 50 micrograms/ml | | 50 micromolar | 100% |
| 50 micrograms/ml | | 50 micromolar | 75% |
| | 30 micromolar | 50 micromolar | 100% |
| | 30 micromolar | 50 micromolar | 75% |
| 50 micrograms/ml | 30 micromolar | 50 micromolar | 100% |
| 50 micrograms/ml | 30 micromolar | 50 micromolar | 75% |

The lipid compositions of in vitro skin substitutes examined to date show significant differences compared to that found in normal human skin. In particular, the levels of ceramides 6 and 7 are greatly reduced in the in vitro cultures. To determine whether preparation of organotypic skin cultures using the culture conditions shown in Table 2 has a synergistic effect on epidermal lipid composition, the lipid profiles of supplemented cultures are compared to lipids isolated from unsupplemented control cultures and to lipids extracted from normal human skin. Lipid profiles of the cultures are determined by high-performance thin-layer chromatography (HPTLC) of lipids extracted from the epidermal culture layers. Organotypic cultures are heated to 60° C. for 1 min to separate the epidermal and dermal layers. Total lipids are extracted from the epidermal layer by sequential extraction with 2 ml chloroform/methanol (1:2), 2 ml chloroform/methanol/water (1:2:0.5), 2 ml chloroform/methanol (1:2), 2 ml chloroform/methanol (2:1) and finally with 2 ml chloroform. Following the addition of 0.2 ml 2.5% KCl and 2 ml water, the samples are centrifuged and the lower phase removed to a clean tube. The remaining upper phase is extracted with 4 ml chloroform. The chloroform extract is combined with the lower phase from the initial extract. Solvents are removed by evaporation under nitrogen and the extracted lipids are dissolved in chloroform/methanol (2:1). Total lipid content in the extracts is determined by weighing samples of the extract after evaporation of solvent.

Extracted lipids (50 micrograms) are applied to silica gel 60 HPTLC plates (Merck, Darmstad, FRG) and resolved by one-dimensional HPTLC using the ceramide development system. Lipid separation is achieved by sequential development of HPTLC plates in chloroform, chloroform/acetone/methanol (76:8:16), chloroform/hexyl acetate/acetone/methanol (86:1:10:4), chloroform/acetone/methanol (76:4:20), chloroform/diethyl ether/hexyl acetate/ethyl acetate/acetone/methanol (72:4:1:4:16:4), and finally with hexane/diethyl ether/ethyl acetate (80:16:4). The TLC plate is dried briefly following each development step before proceeding to the next solvent system. Following separation, lipids are detected by staining with copper acetate and copper sulfate in sulfuric acid followed by charring. Each culture condition is analyzed in triplicate and the levels of specific lipid components quantified by densitometry and expressed as a percentage of total lipid. Previous studies have shown that ceramides 5-7 comprise only 10% of total ceramide mass of in vitro skin substitutes as compared to 39% in normal epidermis. There is a corresponding increase in ceramide 2 in the in vitro cultures, which comprises approximately 50% of total ceramide mass as compared to 22% in normal skin. In preferred embodiments, skin equivalents of the present invention are cultured under conditon that result in an increase in the content of ceramides 5-7 to between 30-45% of total ceramide mass and a reduction of the levels of ceramide 2 to between 20-30% of total ceramide mass.

The ultrastructure of lipid lamellae in organotypic cultures prepared under the conditions described in Table 2 is examined by electron microscopy. Cultures are fixed in 2% glutaraldehyde and 2% formaldehyde in 0.1M cacodylate buffer pH 7.4, then post-fixed in 1% osmium tetroxide followed by 0.25% ruthenium tetroxide. Samples are dehydrated through an ethanol series, embedded in Eponate, and sectioned on a Reichert Ultracut microtome. Sections are stained with uranyl acetate and lead citrate and examined using a Hitachi H-7000 electron microscope (Hitachi, San Jose, Calif.). The organotypic cultures produced by the conditions listed in Table 2 are examined for restoration of the pattern of alternating electron lucent and electron dense lipid lamellae seen in normal skin.

Organotypic cultures are also assessed for cell proliferation and cell-type specific differentiation markers, including involucrin, transglutaminase and keratins.

EXAMPLE 2

Expression of Exogenous Klf4 in NIKS Cells

This Example describes the expression of exogenous Klf4 in NIKS cells. The transcription factor Krüppel-like factor 4 (Klf4) is a zinc-finger protein expressed at high levels in epithelium undergoing terminal differentiation, especially skin and intestinal epithelium. In skin, it is enriched in the mitotically inactive suprabasal layer of the epidermis. Klf4 was identified by low-stringency hybridization with a probe for a zinc-finger domain in a NIH 3T3 cell cDNA library (Shields et al., J. Biol. Chem, 271(33): 20009-17 (1996)). Its three C2H2 zinc fingers relate it to a family of zinc finger transcription factors that includes EKLF and LKLF, factors that are important for tissue-specific differentiation. It is expressed at highest levels in growth-arrested cells and at undetectable levels in proliferating cells. Constitutive expression of Klf4 COS-1 cells inhibits DNA synthesis. It binds to a defined DNA sequence that is important in the regulation of the cytochrome P450 gene CYP1A1 (Zhang et al., J. Biol. Chem., 273(28): 17917-25 (1998)). Binding of Klf4 to its binding site in CYP1A1 inhibits expression of CYP1A1, probably by competing for DNA binding with SP1 and through direct protein-protein interactions with SP1. Recent studies report that Klf4 can also regulate its own expression and that an important binding interaction is with p300/CBP (Geiman et al., Nucleic Acids Res., 28(5): 1106-1113 (2000); Mahatan et al., Nucleic Acids Res., 27(23): 4562-9 (1999)). As is true with other key transcription factors, Klf4 can be a potent activator of some genes and a repressor of others.

Klf4 is currently the best candidate gene for a key regulator of barrier function in the skin. Elimination of Klf4 expression in mice results in neonatal lethality, apparently as a result of excessive water loss through a defective epidermal permeability barrier. These observations suggest that Klf4 regulates genes that are essential for the formation of a normal epidermal permeability barrier and raise the possibility that expression of Klf4 in cultured skin substitutes might improve the barrier function of these cultures. This Example describes two methods of expressing Klf4 in differentiating keratinocytes. The first method is the generation of an inducible expression construct in which expression of human Klf4 is regulated by the presence or absence of the tetracycline derivative, doxycycline, in the culture medium. A second method of directing Klf4 epression in organotypic cultures utilizes a DNA fragment containing either 3.7 kb of the involucrin promoter region, which directs expression in differentiating keratinocytes (Carroll et al., Proc. Natl. Acad. Sci. USA, 90(21): p. 10270-4 (1993)) or 135 bp of the transglutaminase 3 promoter region, which also directs expression in differentiating keratinocytes (Lee et al., J. Biol. Chem., 271(8): 4561-8 (1996)).

The cDNA encoding human Klf4 is isolated by PCR using primers to the known Klf4 sequence (Yet et al., J. Biol. Chem., 273(2): 1026-31 (1998)). The Klf4 cDNA is cloned into the expression vector pTRE2 (Clontech, Palo Alto, Calif.), which contains a minimal CMV promoter flanked by seven repeats of the tet operator (tetO). The integrity of the cloned Klf4 cDNA is verified by sequence analysis using primers derived from the known Klf4 sequence.

Purified DNA from the Klf4 expression plasmid is introduced into NIKS cells along with the pTet-On plasmid (Clontech, Palo Alto, Calif.), which encodes a derivative of the tet repressor protein. This protein, rtTA, binds to the tet operator in the presence of doxycycline and induces expression of Klf4 when doxycycline is present in the culture medium. The gene encoding a protein that confers resistance to blasticidin will be amplified by PCR and cloned into the pTet-On plasmid to allow for selection of stably-transfected cells. Transfected cells are selected by growth in media containing blasticidin (5 micrograms/ml), which will kill any NIKS cells that have not incorporated the plasmids into their genome. Stable cell lines that contain both the pTRE2-Klf4 and pTet-On plasmids are identified by examining multiple clonal cell lines by Southern blot using digoxygenin-labeled probes derived from both the pTet-On and pTRE2 plasmids. Multiple clones that contain intact copies of the pTet-On and pTRE2 plasmids are isolated and examined for expression of the Klf4 transgene in the presence of doxycycline.

To examine expression from the Klf4 transgene, monolayer cultures of stably-transfected cell lines and control untransfected cells are incubated in medium containing doxycycline (1 microgram per ml). Total RNA is then isolated from cultures at multiple time points after doxycycline addition using Trizol Reagent (Life Technologies, Rockville, Md.). Twenty micrograms of total RNA is analyzed by Northern blot hybridization using digoxygenin-labeled probes derived from the cloned Klf4 cDNA and detected using the Genius non-radioactive detection system (Roche Molecular Biochemicals, Indianapolis, Ind.). RNA is also isolated from transfected cultures grown in the absence of doxycycline to determine the basal level of Klf4 expression from the transgene. RNA isolated from untransfected cells at each time point will be analyzed to establish a background level of Klf4 expression from the endogenous Klf4 gene.

The Klf4 cDNA is also cloned into an expression plasmid containing promoter sequences from the involucrin gene. A DNA fragment containing 3.7 kb of the involucrin promoter directs transgene expression to the suprabasal layers of the epidermis. This promoter fragment is amplified from total genomic DNA by PCR using primers to the known INV promoter sequence (Lopez-Bayghen et al., J. Biol. Chem., 271(1): 512-520 (1996)). The Klf4 cDNA is cloned into a plasmid containing this involucrin promoter fragment and used to generate stable cell lines of NIKS that contain this transgene. Stable cell lines are selected by co-transfecting NIKS cells with the INV/Klf4 plasmid and a plasmid expressing the blasticidin resistance gene and growing the transfected cells in the presence of blasticidin. Multiple blasticidin-resistant cell lines will be isolated and examined by Northern blot for increased Klf4 expression as compared to cells transfected only with the blasticidin-resistance plasmid. While the involucrin promoter has been used successfully to direct expression of several transgenes to the differentiating epidermis, it is possible that the INV/KLF4 construct will not be expressed to high enough levels or in the proper temporal or spatial pattern to have an effect on barrier function. If Klf4 expression from the involucrin promoter construct is not readily detected, expression constructs are generated containing the promoter regions of another keratinocyte-specific gene, transglutaminase 3. The Klf4 cDNA is cloned into an expression plasmid containing promoter sequences from the transglutaminase 3 (TG3) gene. A TG3 promoter fragment containing 126 bp upstream and 10 bp downstream from the transcription start site directs transgene expression to epithelial cells (Lee et al., J Biol Chem, 271(8): 4561-8 [1996]).

The Klf4 cDNA is cloned into a plasmid containing this TG3 promoter fragment and generate stable cell lines of NIKS that contain this transgene. Stable cell lines are selected by co-transfecting NIKS cells with the TG3/Klf4 plasmid and a plasmid expressing the blasticidin resistance gene and growing the transfected cells in the presence of blasticidin. Multiple blasticidin-resistant cell lines are isolated and examined by Northern blot for increased Klf4 expression as compared to cells transfected only with the blasticidin-resistance plasmid.

Stable NIKS cell lines that express Klf4 from the involucrin promoter or the doxycycline-inducible system are examined in organotypic culture to confirm that Klf4 is expressed under these culture conditions. Standard media and procedures for organotypic cultures are described in Example 1. Klf4-expressing NIKS cells are seeded onto a contracted collagen matrix containing fibroblasts and grown in submerged culture for 4 days before being lifted to the air interface. Organotypic cultures are fed cornification medium every 3 days and maintained at the air/liquid interface for 14 days to form a stratified epithelium. Cultures with NIKS expressing Klf4 from the inducible promoter are grown in media containing 1 microgram/ml doxycycline. Total RNA is isolated from organotypic cultures by homogenizing the epidermal layer in Trizol reagent, extracting the homogenate with chloroform, and precipitating total RNA with isopropanol. RNA is examined for Klf4 expression as described above for monolayer cultures.

The effects of Klf4 expression on barrier function are examined by surface capacitance measurement, lipid composition and ultrastructure of the organotypic cultures by the methods described in Example 1. In addition, some of the agents to be added to the cultures in Example 1, especially the PPAR and FXAR activators, may serve to activate other regulatory genes that act in concert with Klf4. This hypothesis is supported by the ability of these agents to accelerate the in utero development of barrier function.

Data on the timing and extent of Klf4 expression using the two expression systems described herein will allow for the design of strategies to enhance barrier function by regulating Klf4 expression in NIKS organotypic cultures. The NIKS organotypic cultures have been extensively characterized for ultrastructure and expression of key differentiation markers. Examination of these phenotypic properties of the culture in the presence of added Klf4 expression will provide additional clues to the consequences of Klf4 expression.

EXAMPLE 3

Secretion of IL-1α in Response to Skin Irritants

This example demonstrates that NIKS cells secrete IL-1α in response to skin irritants. To determine whether organotypic cultures of NIKS cells exhibit irritant responses typical of primary keratinocytes, NIKS skin equivalent cultures were exposed to concentrations of SDS that are known to elicit skin irritant responses in vivo and in vitro. Solutions of SDS (0.1%, 0.2%, and 0.5%) were topically applied to air-exposed NIKS organotypic cultures and incubated for 24 hr at 37° C. After 24 hr, the media underneath the cultures was assayed for IL-1α protein using a Quantikine IL-1α ELISA kit (R&D Systems, Minneapolis, Minn.) and cultures were incubated with MTS reagent (Promega Corp., Madison, Wis.) to determine cell viability. The concentrations of IL-1α in media from control and SDS-treated cultures are shown in FIG. 3. Media from untreated cultures contained 25 pg/ml IL-1α, whereas the concentration of IL-1α in cultures treated with 0.1%, 0.2% or 0.5% SDS was 290, 375 and 275 pg/ml respectively.

These values correspond well with published IL-1α responses in SDS-exposed skin equivalents (Perkins et al., Toxicological Sciences, 48:218 [1999]). The decrease in IL-1α secretion in cultures treated with 0.5% SDS is likely due to decreased cell viability in these cultures as detected by an MTS assay.

EXAMPLE 4

Generation of Reporter Gene Constructs

This example describes methods for generating NIKS cells comprising reporter gene constructs comprising IL-8 promoter fragments. Using primers to the known sequence, PCR is used to amplify a 1.5 kb DNA fragment containing the IL-8 promoter and flanking sequences. After verification of the amplified DNA by sequence analysis, this DNA fragment is cloned into the expression vector pSEAP (Tropix, Bedford, Mass.), which contains the coding region for SEAP but which lacks regulatory elements to drive its expression. The integrity of the reporter construct is verified by restriction analysis and DNA sequencing.

Initially experiments to determine whether the IL-8/SEAP reporter construct is inducible by irritants are performed with transiently-transfected NIKS cells. Pools of transfected cells are exposed to known irritants (e.g., SDS, trans-retinoic acid) and to control substances (e.g., mineral oil, water) and the amount of SEAP activity is determined by chemiluminescence at 4, 8 and 24 hr after irritant exposure. SEAP activity is detected by incubation of media from transfected cells with a chemiluminescent substrate (Phospha-light, Tropix, Bedford, Mass.) using a microplate luminometer. Analysis of IL-8/SEAP reporter gene expression is performed in triplicate using independently transfected cell populations.

Expression of RNA from the IL-8/SEAP reporter is compared with increases in the mRNA from the endogenous IL-8 gene. In parallel with the SEAP assays described above, RNA is isolated from identically-treated cultures using Trizol reagent (Life Technologies, Rockville, Md.). As an independent measurement of IL-8 expression in irritant-treated keratinocytes, cultures of primary keratinocytes from pooled donors are treated with the irritants and processed for RNA purification. Total RNA is examined by Northern blot for increased expression of the endogenous IL-8 gene using a PCR fragment amplified based on known sequences. The level of SEAP mRNA expressed from the IL-8/SEAP transgene is also quantified by Northern analysis. Increases in SEAP activity, as measured by chemiluminescence, and SEAP mRNA, determined by Northern blot, are compared to increases in IL-8 mRNA to determine whether expression of the SEAP reporter accurately reflects the induction of IL-8 in response to irritants.

Expression of IL-8 mRNA increases 7 to 40-fold following 24 hr exposure to various skin irritants (de Brugerolle de Fraissinette et al., supra). The reporter construct is judged to be irritant-inducible if the level of SEAP activity and mRNA increase at least 5-fold in irritant-treated cultures.

If SEAP activity is increased in transfected NIKS cells following irritant exposure, stable cell lines are generated with the IL-8/SEAP reporter construct as follows. NIKS cells are co-transfected with the IL-8/SEAP reporter construct and a plasmid that confers resistance to blasticidin (pCMV/bsd Invitrogen, Carlsbad, Calif.). Transfected cells are grown in the presence of blasticidin to select for stably-transfected cells. Individual clones of transfected cells are examined for expression of the IL-8/SEAP reporter gene in response to irritants. Clones that display irritant-inducible transgene expression are used to generate organotypic skin cultures. These cultures are examined for irritant-responsiveness by topical application of SDS, trans-retinoic acid, and negative controls (water, mineral oil) as described above. The organotypic cultures may also be mechanically disrrupted, lysed in buffer containing a non-ionic detergent, and assayed for SEAP activity.

Because the 1.5 kb fragment of the IL-8 regulatory region may not contain all of the regulatory elements necessary for full responsiveness, it is possible that the magnitude of the reporter gene response may be less than that observed with the endogenous IL-8 gene. If this fragment is insufficient to direct irritant-specific expression of SEAP, the PCR product is used as a probe to screen a genomic DNA library. This approach allows one to recover larger DNA fragments that are likely to contain more of the IL-8 regulatory region. These DNA fragments are characterized by restriction mapping and sequence analysis. DNA fragments containing between 5 and 10 kb of genomic DNA flanking the IL-8 promoter are cloned into the pSEAP vector and examined for the ability to direct irritant-inducible SEAP expression as described above.

Alternative reporter gene constructs are also generated using a DNA fragment containing the regulatory region of another irritant-inducible cytokine, IL-1α. Published sequences for this gene include 1437 bp of DNA upstream from the transcription start site (Furutani et al., Nuc. Acid Res. 14:3167 [1986]). A DNA fragment containing these sequences has been used to direct expression of a CAT reporter gene in response to viral transactivators (Mori and Prager, Blood 87:3410 [1996]). This fragment contains two binding sites for NF-κB, a transcription factor that is involved in gene expression changes in response to skin irritants (Corsini et al., J. Invest Dermatol. 108:892 [1997]).

Additionally, a NIKS cell line reporter gene construct is also generated by introducing a reporter gene construct into the endogenous IL-8 locus in NIKS cells. This "knock-in" strategy has been utilized to accurately reproduce proper temporal and spatial expression of reporter genes (Elefanty et al., Proc Natl Acad Sci USA, 95:11897 [1998]; Morrison et al., Mech Dev, 1999. 84169 [1999]; Jin et al., Biochem Biophys Res Commun, 270:978 [2000]).

EXAMPLE 5

Identification of Irritant-Responsive Genes

This example describes experiments useful for the identification of novel genes whose expression is induced by irritant exposure. Genome Systems cDNA microarray (GEM microarrays; Incyte Genomics, Palo Alto, Calif.) are used for the analysis of gene expression. All manipulations are performed by Incyte Genomics. A UniGEM V 2.0 Microarray, built from Incyte's sequence verified cDNA clones and containing 8514 unique human cDNAs is used. Larger arrays are used as they become available. In vitro skin equivalent cultures are prepared using cultured human keratinocytes from pooled adult donors (available from Clonetics, Walkersville, Md.). Cultured keratinocytes are seeded onto a dermal equivalent consisting of dermal fibroblasts embedded in a contracted collagen matrix and the resulting organotypic culture is lifted to the air interface to induce differentiation and stratification of the keratinocyte layer. After 14 days, organotypic cultures are treated topically with known irritants (e.g., 0.2% SDS, 0.005% calcipotriol, 0.025% trans-retinoic acid) or non-irritant controls (e.g., mineral oil, vaseline) for 24 hr. These compounds all induce expression and secretion of the pro-inflammatory cytokines IL-1α and IL-8 in irritant-treated skin equivalents (de Brugerolle de Fraissinette et al., supra).

Purification of mRNA from organotypic cultures is carried out using known procedures. The epidermal layer of control and irritant-exposed organotypic cultures is mechanically dislodged from the collagen dermal equivalent and placed in Trizol reagent (Life Technologies, Rockville, Md.) for 1 hr. Following periodic vortexing and pipetting to break apart the tissue, RNA is separated from cellular protein and DNA by phenol-chloroform extraction. The aqueous phase from this extraction is then treated with ethanol to precipitate total RNA. Poly $A^+$ mRNA is isolated from total cellular RNA using the Oligotex mRNA purification system (Qiagen, Valencia, Calif.).

To verify the that treated cultures exhibit an irritant response, equal amounts of mRNA from control and irritant-treated cultures are examined by Northern blot for induction of the known irritant-responsive genes IL-1α and IL-8. RNA from cultures that exhibit induction of IL-1α and IL-8 expression are compared to RNA from control cultures by gene expression profiling to identify novel irritant-responsive genes. Purified mRNA is dissolved in TE buffer at a concentration of 50 ng/μl and shipped to Incyte Genomics for cDNA microarray analysis. Data analysis is performed using the GEMTools Software from Genome Systems and cluster analysis programs available from the MIT Center for Genome Research and the laboratory of Patrick O. Brown at Stanford University.

Genes identified as irritant responsive are utilized in reporter gene assays using the methods described in Example 4 above.

EXAMPLE 6

Lipid Content of Skin Equivalents

This example describes the preparation of skin equivalents with optimized serum-free medium and a second set of skin equivalents prepared with sub-optimal medium. Subsequently, the lipid content of the resulting cultures was determined.

Organotypic cultures were initiated by plating 350,000 NIKS cells onto dermal equivalents previously prepared within a 10 mm MILLICELL insert. The media used to complete this step was comprised of a base medium [3:1 mixture of Ham's F12 medium/Dulbecco's modified Eagle's medium (DME), supplemented with 24 μg/ml adenine, 8.3 ng/ml cholera toxin, 5 μg/ml insulin, 0.4 μg/ml hydrocortisone, with the final calcium concentration adjusted to 1.88 mM] supplemented with 0.2% Fetal Clone II (a calf serum substitute).

Two days post-plating, the organotypic cultures were supplied with fresh medium to maintain growth. Cultures were supplied with either base medium supplemented with 0.2% Fetal Clone II or base medium supplemented with 0.2% Fetal Clone II and additional constituents (1 mg/ml endotoxin-free BSA, 1 ng/ml epidermal growth factor, 50 μg/ml ascorbic acid, 1 μM isoproterenol, 10 μM carnitine, 10 μM serine, 25 μM oleic acid, 15 μM linoleic acid, 7 μM arachidonic acid and 1 μM α-tocopherol).

Four days post-lifting, and every other day for the remainder of the culture period, the cultures were supplied with optimal medium (base medium supplemented with 1 mg/ml endotoxin-free BSA, 1 ng/ml epidermal growth factor, 50 μg/ml ascorbic acid, 1 μM isoproterenol. 10 μM carnitine, 10 μM serine, 25 μM oleic acid, 15 μM linoleic acid, 7 μM arachidonic acid and 1 μM α-tocopherol) or a sub-optimal medium (base medium supplemented with 1 mg/ml endotoxin-free BSA, 1 ng/ml epidermal growth factor, 10 μM carnitine and 10 μM serine).

At the completion of the culture period, total lipids were extracted from the cultures and resolved by high-performance thin-layer chromatography (HPTLC). Following separation, the plates were charred and the resulting chromatograms were scanned by densitometry to quantify individual lipid species. The cultures grown in optimized culture medium contained a higher percentage of total ceramides than cultures grown in sub-optimal medium (Table 3). In addition, the cultures grown in optimal medium contained much higher levels of the polar ceramides 3, 4, 5, and 6 than cultures grown under sub-optimal conditions.

TABLE 3

Ceramide content of skin cultures

|  | Optimal media | Sub-optimal media |
| --- | --- | --- |
| Cer 6II |  | 0.07% |
| Cer 6I | 0.41% | 0.03% |
| Cer 4/5 | 1.31% | 0.46% |
| Cer 3 | 1.37% | 0.44% |
| Cer 2 | 2.09% | 1.69% |
| Cer 1 | 1.33% | 0.42% |
| Total ceramide | 6.52% | 3.11% |

EXAMPLE 7

Expression of GKLF in NIKS Cells

This example describes the expression in NIKS cells of GKLF, a protein thought to mediate barrier function development in mice.

DNA encoding the GKLF protein was isolated by PCR and cloned into an expression vector containing the human involucrin promoter. After verification of the GKLF and involucrin fragments by DNA sequencing, the constructs were introduced into NIKS cells by transfection. Twenty-four hours after transfection, total RNA was isolated from the transfected cells and expression of GKLF in these cells was examined by reverse-transcription/PCR (RT-PCR).

A PCR product corresponding to spliced GKLF mRNA was detected in RNA from cells transfected with the involucrin/GKLF construct, but not in control RNA from cells transfected with empty vector. In addition, the GKLF PCR product was not detected in reactions from which reverse transcriptase was omitted. These results demonstrate that GKLF mRNA was expressed in transfected NIKS cells.

In a second set of experiments, DNA encoding GKLF was cloned into the pTRE2 vector, which allows for inducible expression of GKLF following addition of doxycycline. After verification of the GKLF and involucrin fragments by DNA sequencing, the constructs were introduced into NIKS cells by transfection. Eight hours after transfection, doxycycline was added to half of the transfected cultures and all cultures were incubated for an additional 16 hours. Twenty-four hours after transfection, total RNA was isolated from the transfected cells and expression of GKLF in these cells was examined by reverse-transcription/PCR (RT-PCR). A PCR product corresponding to spliced GKLF mRNA was observed in samples with and without doxycycline, but more product was seen in samples following doxycycline addition. No PCR products were detected in reactions from which reverse transcriptase was omitted. These results demonstrate inducible expression of GKLF mRNA in transfected NIKS cells.

EXAMPLE 8

Culture Methods

This example describes culture methods common to the following Examples.

Media. The organotypic culture process uses six different culture media: 3T3 feeder cell medium (TM); fibroblast growth medium (FM); NIKS medium (NM); plating medium (PM); stratification medium A (SMA); and stratification medium B (SMB). TM is used to propagate 3T3 cells that act as feeder cells for NIKS cells in monolayer culture. TM is a mixture of Dulbecco's modified Eagle's medium (DME, GibcoBRL) supplemented with 10% calf serum (Hyclone). FM is a mixture of Ham's F-12 medium (GibcoBRL) and 10% Fetal Clone II (Hyclone) serum. NM is used to grow NIKS keratinocytes. NM is a 3:1 mixture of Ham's F-12 medium (GibcoBRL) and DME supplemented with 2.5% Fetal Clone II (Hyclone), 0.4 µg/ml hydrocortisone (Calbiochem), 8.4 ng/ml cholera toxin (ICN), 5 µg/ml insulin (GibcoBRL), 24 µg/ml adenine (Sigma) and 10 ng/ml epidermal growth factor (EGF, R&D systems). PM is the medium used when NIKS cells are seeded onto a dermal equivalent. PM is the same as NM except that EGF is removed, $CaCl_2$ (Sigma) is supplemented to a final calcium concentration of 1.88 mM, and only 0.2% Fetal Clone II serum is added. SMA is the same as PM with the addition of 1 mg/ml bovine serum albumin (BSA), 1 µM isoproterenol, 10 µM carnitine, 10 µM serine, 25 µM oleic acid, 15 µM linoleic acid, 7 µM arachidonic acid, 1 µM α-tocopherol, 0.05 mg/ml ascorbic acid (all from Sigma), and 1 ng/ml EGF. SMB is used during the epidermal stratification phase of STRATATEST skin equivalent and STRATAGRAFT skin equivalent growth. SMB is the same as SMA but without the presence of the Fetal Clone II serum supplement.

Feeder preparation. Prior to starting STRATATEST skin equivalent or STRATAGRAFT skin equivalent organotypic cultures, 3T3 feeder cells are prepared and then used either fresh or frozen for later use. 3T3 cells are grown to confluence and treated with mitomycin-C (4 ug/ml of mitomycin-C in TM, Roche) for two hours. The cells are then washed, resuspended, and plated at a density of $1.25 \times 10^6$ per 100 mm tissue culture dish to support NIKS growth. If frozen feeders are used, a single frozen ampoule containing 1 ml with $2.5 \times 10^6$ is thawed, diluted with fresh TM and plated onto one or more 100 mm tissue culture dishes. This is done for as many dishes as will be needed for NIKS cell growth one day prior to plating the NIKS cells.

Dermal equivalent preparation. Frozen NHDF cells are thawed and plated. The cells are fed FM the next day to remove residual cryoprotectant and subsequently to maintain cell growth. Preconfluent NHDF cells are harvested for use in the dermal equivalent. To prepare the dermal equivalent, rat tail tendon collagen (Type I, Becton-Dickinson) is first diluted to 3 mg/ml in 0.03N acetic acid and chilled on ice. A mixture of concentrated Ham's F12 medium (8.7× normal strength, buffered with HEPES at pH 7.5) is mixed with Fetal Clone II. These two solutions are 11.5 and 10% of the final solution volume. 1 N NaOH is added to the medium mixture (2.5% of final solution). The diluted collagen (74%) is then added to the mixture. A 2% volume of suspended fibroblasts ($2.5 \times 10^6$ cells/ml for the dermal equivalent of STRATATEST and $1 \times 10^6$ for dermal equivalent of STRATAGRAFT) is added to the mixture. The solution is mixed gently but thoroughly. 100 µl is aliquoted into tissue culture inserts (MILLICELL from Millipore Corp.) placed 25 in a 100 mm tissue culture dish for STRATATEST. The STRATAGRAFT skin equivalent uses TRANSWELL inserts from Corning. A 13 ml dermal equivalent is poured into each insert making it roughly three times the thickness of a STRATATEST dermal equivalent. After 30 minutes for gel formation, the dish containing STRATATEST dermal equivalents is flooded with 20 ml of FM. One or two drops FM are placed on the surface of each STRATATEST dermal equivalent. For STRATAGRAFT dermal equivalents, 80 ml of FM is placed around the TRANSWELL insert in a 150 mm tissue culture dish and 10 ml is placed on top of the dermal equivalent. The inserts are placed in 37° C., 5% $CO_2$, 90% relative humidity incubator until used. One day prior to seeding the dermal equivalents with NIKS cells, they are lifted to the air interface by placing them onto a sterile stainless steel mesh with two wicking pads (S&S Biopath) on top to supply medium through the bottom of the tissue culture insert.

NIKS Growth and Seeding. Feeders are prepared fresh or thawed and plated in TM one day prior to NIKS plating. NIKS cells are plated onto the feeders at a density of approximately $3 \times 10^5$ cells per 100 mm dish. If the NIKS cells are newly thawed, they are fed fresh NM one day post-plating to remove residual cryoprotectant. The NIKS cells are fed NM to maintain growth as required. When cell approach confluence, the NIKS cells are harvested, counted, and resuspended in PM. $4.65 \times 10^5$ NIKS cells/$cm^2$ are seeded onto the surface of the MIILLICELL or TRANSWELL dermal equivalents, which have been lifted to the air interface for one day. The dishes are fed PM to flood underneath the metal lifter and placed back into the incubator. Two days later, the cultures are fed SMA. After an additional two days, the cultures are fed SMB and transferred to a 75% humidity incubator where they remain, maintained with additional SMB feedings, until mature.

EXAMPLE 9

This example describes the preparation of dermal equivalents using 1 mg/ml collagen. Briefly, 24 ml Ham's F12 medium prepared at 10× concentration was mixed with 4.8 ml sterile $H_2O$, 2.4 ml Penicillin/Streptomycin mixture and 24 ml Fetal Clone II in a 50 ml conical tube. Rat tail tendon collagen Type I (1.46 ml) at 4.11 mg/ml was diluted with 1.882 ml sterile $H_2O$ and 2.658 ml of 0.05% acetic acid. Normal human dermal fibroblasts were harvested from culture and resuspended at a cell density of $10^6$ and $10^4$ cells/ml. 0.815 ml of the medium-containing mixture was combined with 2.619 ml of diluted collagen and 34 µl of fibroblasts at $10^4$ cells/ml. 116.5 µl of this mixture was aliquotted into tissue culture inserts (25 of which are in a Petri dish) and allowed to gel for 15 minutes at 37° C. An additional 0.815 ml of the medium-containing mixture was combined with another 2.619 ml of diluted collagen and 137 µl of fibroblasts at $10^6$ cells/ml. 116.5 µl of this mixture was aliquotted into the tissue culture inserts on top of the previous gel and allowed to gel for 30 minutes.

The petri dish was then flooded with 20 ml of FM medium and incubated for 5 days. The FM was then removed and the liquid aspirated from the surfaces of the dermal equivalents. NIKS cells were harvested using standard procedures, resuspended at $2.345 \times 10^6$ cells/ml in plating medium (PM). 150 µl of this suspension was put on the surface of each dermal equivalent and allowed to incubate for 2 hours. The seeded dermal equivalents were then flooded with 20 ml PM. After two days the submerged cultures were refed with PM.

After two more days the medium was removed from the petri dish as well as from the surface of the cultures. The cultures were lifted to the air interface and fed approximately 30 ml of PM supplemented to 2% serum every 2 days. Cultures were analyzed 14 days after they were seeded. None of the cultures had complete epidermal coverage of the dermal equivalent. Thus they were unsuitable for commercial application.

EXAMPLE 10

This example describes the preparation of dermal equivalents using 3 mg/ml collagen. 4.785 ml Ham's F12 medium prepared at 10× concentration was mixed with 0.946 ml sterile $H_2O$, 0.473 ml Penicillin/Streptomycin mixture, and 4.785 ml Fetal Clone II in a 50 ml conical tube. 4.6 ml of this medium mixture was mixed with 0.242 ml sterile $H_2O$ and 0.289 ml 1N NaOH. 0.92 ml of the mixture was mixed with 3 ml rat tail tendon collagen Type I at 3.11 mg/ml. To this was added 186 µl of a human dermal fibroblast suspension at $10^6$ cells/ml. 100 µl of this mixture was placed into the MILLI-CELL inserts (1 cm diam) and allowed to gel for 30 minutes. The petri dish was then flooded with 20 ml of FM medium and allowed to incubate. After 5 days, the FM was removed and the liquid aspirated from the surfaces of the dermal equivalents. NIKS™ cells were harvested using standard procedures, resuspended at $2.345 \times 10^6$ cells/ml in plating medium (PM). 150 µl of this suspension was put on the surface of each dermis and allowed to incubate for 2 hours. The seeded dermal equivalents were then flooded with 20 ml PM. After two more days the medium was removed from the petri dish (including the surface of the cultures) and the cultures were lifted to the air interface and fed approximately 30 ml of stratification medium every 2 days. Cultures were analyzed 14 days after they were seeded. At the completion of culture growth, all of the cultures had complete coverage of the dermal equivalent with epidermis and were smooth and dry in appearance. Thus they were highly acceptable for commercial application.

EXAMPLE 11

This example demonstrates the beneficial effects of prelifting the dermal equivalent prior to seeding with keratinocytes. 1.31 ml Ham's F12 medium prepared at 10× concentration was mixed with 0.328 ml sterile $H_2O$, 0.148 ml Penicillin/Streptomycin mixture, and 1.472 ml Fetal Clone II in a 50 ml conical tube and 1.63 ml (~half) was split into a second tube. 2.92 ml of rat tail tendon collagen (4.11 mg/ml) was mixed with 3.764 ml sterile $H_2O$, and 5.316 ml of 0.05% acetic acid to give 1 mg/ml collagen in 0.05% acetic acid. 5.24 ml of the diluted collagen was added to 1.63 ml of the medium mixture. 74 µl of human dermal fibroblast cells harvested with standard protocols at a cell density of $10^4$ cells/ml was added and gently mixed. 116.5 µl of this mixture was aliquotted into tissue culture inserts (25 to a Petri dish) and allowed to gel for 15 minutes at 37° C. Another 5.24 ml of collagen was added to the second 1.63 ml of medium mixture along with 274 µl of fibroblasts at $10^6$ cells/ml. 116.5 µl was added to each insert on top of the first gelled collagen layer. This was allowed to gel for 30 minutes at 37° C. The petri dishes were then flooded with 20 ml of FM so that the dermal equivalents could mature submerged in medium. After four days the medium was removed from the petri dish (including from the surface of the cultures) and the cultures were lifted to the air interface and fed approximately 30 ml of FM. The cultures were left in the incubator in this state overnight. Then they were seeded with 150 µl of NIKS keratinocytes harvested from monolayer culture using standard protocols at a cell density of $2.345 \times 10^6$ cells/ml. After seeding, the cultures were fed PM and returned to the incubator. Two days later, the cultures were fed with SMA, and every second day thereafter cultures were fed with SMB for a total of eight feedings. At the completion of culture growth, all of the cultures had complete coverage of the dermal equivalent with epidermis and were smooth and dry in appearance. Histology revealed that the prelifted samples had approximately equal thicknesses of dermis and epidermis, and all stratified layers were present in the epidermis.

EXAMPLE 12

This example describes the effect of prelifting for the entire life of the dermal equivalent. Cultures were prepared exactly as in the successful experiment listed above, with the exception that they were never submerged. The gels were poured with the MILLICELL inserts lifted to the air interface and all subsequent seeding and feeding took place with the cultures lifted. At the completion of culture growth, one in ten of the cultures had complete coverage of the dermal equivalent with epidermis. This effect is apparently due in part to poor adherence of the dermal equivalent to the bottom of the MILLI-CELL insert since the dermal equivalent had pulled away from the sides in most samples. Histology indicated that the dermal and epidermal layer thicknesses were highly variable. Likewise epidermal stratification ranged from well differentiated to only monolayer coverage which was unacceptable for commercial use.

EXAMPLE 13

This example describes the optimization of a serum-free media that supports full stratification of keratinocytes in organotypic culture that also results in skin equivalents with improved barrier function.

Organotypic cultures were initiated by plating 350,000 NIKS cells onto a dermal equivalent previously prepared within a 10 mm MILLICELL insert. The media used to complete this step was comprised of a base medium (3:1 mixture of Ham's F12 medium/Dulbecco's modified Eagle's medium (DME), supplemented with 24 µg/ml adenine, 8.3 ng/ml cholera toxin, 5 µg/ml insulin, 0.4 µg/ml hydrocortisone, 100 units/ml penicillin, 100 µg/ml streptomycin, with final calcium concentration adjusted to 1.88 mM through the addition of $CaCl_2$) supplemented with 0.2% Fetal Clone II.

Two days post-plating, the organotypic cultures were supplied with fresh media to maintain growth. Cultures were supplied with either base media supplemented with 0.2% Fetal Clone II or base media with additional constituents (1 mg/ml low endotoxin bovine serum albumin, 1 ng/ml epidermal growth factor, 1 µM isoproterenol, 10 µM carnitine, 10 µM serine, 25 µM oleic acid, 15 µM linoleic acid, 7 µM arachidonic acid, 1 µM α-tocopherol, and 0.05 mg/ml ascorbic acid) supplemented with 0.2% Fetal Clone II.

Four days post-plating, and for the remainder of the experiment, the organotypic cultures were supplied with one of six media formulations. Cultures that had previously received base media supplemented with 0.2% Fetal Clone II, were supplied with either base media without Fetal Clone II supplementation, or base media supplemented with 0.2% Fetal Clone II, or base media supplemented with 2% Fetal Clone II. Cultures that had previously received base media with additional constituents supplemented with 0.2% Fetal Clone II, were supplied with either base media with additional constituents without Fetal Clone II supplementation, or base media with additional constituents supplemented with 0.2% Fetal Clone II, or base media with additional constituents supplemented with 2% Fetal Clone II.

Three criteria were used to evaluate the impact of the media formulations. Visual inspection was used to determine the extent of contiguous cellular surface coverage. Impedance meter readings were used to measure the resulting barrier function of cultures. Viability of tissue post-exposure to 0.1% SDS was used as a practical evaluation of barrier function. For all criteria, organotypic cultures maintained in base media with additional constituents performed better than base media without additional constituents. The exclusion of serum did not hinder the performance of organotypic cultures as long as additional constituents were supplied.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

What is claimed is:

1. A composition comprising 0.1-10.0 mg/ml bovine serum albumin, 0.1-10.0 μM isoproterenol, 1.0-100.0 μM carnitine, 1.0-100.0 μM serine, 1.0-100.0 μM oleic acid, 1.0-100.0 μM linoleic acid, 1.0-100.0 μM arachidonic acid, 0.1-10.0 μM α-tocopherol, 0.005-5.0 mg/ml ascorbic acid, and 0.1-10.0 ng/ml epiderinal growth factor.

2. The composition of claim 1, further comprising serum.

3. The composition of claim 1, further comprising calcium chloride, hydrocortisone, cholera toxin, insulin and adenine.

4. A kit comprising the a container containing the composition of claim 1 and a human skin equivalent.

* * * * *

UNITED STATES PATENT AND TRADEMARK OFFICE
CERTIFICATE OF CORRECTION

PATENT NO. : 7,541,188 B2  Page 1 of 1
APPLICATION NO. : 11/006014
DATED : June 2, 2009
INVENTOR(S) : Paul Barth Conrad, Cathy Ann-Rasmussen Ivarie and Lynn Allen-Hoffman It is certified that error appears in the above-identified patent and that said Letters Patent is hereby corrected as shown below:

IN THE TITLE PAGE:

Item (75) In the Inventors Names, column 1, line 4 please replace "Rusmussen" with --Rasmussen--.

IN THE CLAIMS:

Column 55, Claim 1, line 67 please replace "epiderinal" with --epidermal--; and
Column 56, Claim 4, line 64 after comprising please delete "the".

Signed and Sealed this

Twenty-eighth Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,541,188 B2 | Page 1 of 1 |
| APPLICATION NO. | : 11/006014 | |
| DATED | : June 2, 2009 | |
| INVENTOR(S) | : Paul Barth Conrad et al. | |

It is certified that error appears in the above-identified patent and that said Letters Patent is hereby corrected as shown below:

In the Specification

At Column 1, lines 3-12, please replace:

"This is a divisional application of co-pending U.S. Patent Application Ser. No. 10/087,641, filed March 1, 2002, which claims priority to U.S. provisional patent applications serial numbers 60/287,898, filed 5/01/2001, and 60/273,034, filed 3/02/2001, the specifications of which are herein incorporated by reference in its entireties. This patent application was supported in part by NIH SBIR grants 1 R43 AR47499-01 and 1 R43 ES10692-01A1. The government has certain rights in the invention."

with

--CROSS-REFERENCE TO RELATED APPLICATIONS

This is a divisional application of co-pending U.S. Patent Application Ser. No. 10/087,641, filed March 1, 2002, which claims priority to U.S. provisional patent applications serial numbers 60/287,898, filed 5/01/2001, and 60/273,034, filed 3/02/2001, the specifications of which are herein incorporated by reference in its entireties.

STATEMENT REGARDING FEDERALLY SPONSORED RESEARCH OR DEVELOPMENT:

This invention was made with government support under SBIR grants 1 R43 AR47499-01 and 1 R43 ES10692-01A1 awarded by the National Institutes of Health. The government has certain rights in the invention.--

Signed and Sealed this
Seventeenth Day of June, 2014

Michelle K. Lee
*Deputy Director of the United States Patent and Trademark Office*

```
                          SEQUENCE LISTING

<160> NUMBER OF SEQ ID NOS: 3

<210> SEQ ID NO 1
<211> LENGTH: 2908
<212> TYPE: DNA
<213> ORGANISM: Mus musculus

<400> SEQUENCE: 1
gacgccaaga gagcgagcgc ggctccgggc gcgcggggag cagaggcggt ggcgggcggc      60
gggggcaccc ggagccgccg agtgcccctc cccgcccctc cagcccccca cccaggaacc     120
cgcccgtgac ccgcgcccat ggccgcgcgc acccggtaca gtccccagga ctccgcaccc     180
cgcgccaccg tccagctcgc agttccgcgc caccgcggcc attctcacct ggcggcgccg     240
cccgccaccg cccggaccac agccccgcg ccgccgacag ccacagtggc cgcgacaacg      300 gtggggaca ctgctgagtc caagagcgtg cagcctggcc atcggaccta cttatctgcc      360
ttgctgattg tctattttta taagagttta caactttctct aagaattttt gtatacaaag     420 gaacttttt taaagacatc gccggtttat attgaatcca aagaagaagg atctcgggca      480
atctgggggt tttggtttga ggttttgttt ctaaagtttt taatcttcgt tgactttggg     540
gctcaggtac ccctctctct tcttcggact ccggaggacc ttctgggccc ccacattaat     600
gaggcagcca cctggcgagt ctgacatggc tgtcagcgac gctctgctcc cgtccttctc     660
cacgttcgcg tccggcccgg cgggaaggga gaagacactg cgtccagcag gtgccccgac     720
taaccgttgg cgtgaggaac tctctcacat gaagcgactt cccccacttc ccggccgccc     780
ctacgacctg gcggcgacgg tggccacaga cctggagagt ggcggagctg gtgcagcttg     840
cagcagtaac aacccggccc tcctagcccg gagggagacc gaggagttca acgacctcct     900
ggacctagac tttatccttt ccaactcgct aacccaccag gaatcggtgg ccgccaccgt     960
gaccacctcg gcgtcagctt catcctcgtc ttccccggcg agcagcggcc ctgccagcgc    1020
gccctccacc tgcagcttca gctatccgat ccgggccggg ggtgacccgg gcgtggctgc    1080
cagaaacaca ggtggagggc tcctctacag ccagaatct gcgccacctc ccacggcccc     1140
cttcaacctg ggggacatca atgacgtgag cccctcgggc ggcttcgtgg ctgagctcct    1200
gcggccggag ttggacccag tatacattcc gccacagcag cctcagccgc caggtggggg    1260
gctgatgggc aagtttgtgc tgaaggcgtc tctgaccacc cctggcagcg agtacagcag    1320
cccttcggtc atcagtgtta gcaaaggaag cccagacggc agccaccccg tggtagtggc    1380
gccctacagc ggtggcccgc cgcgcatgtg ccccaagatt aagcaagagg cggtcccgtc    1440
ctgcacggtc agccggtccc tagaggccca tttgagcgct ggaccccagc tcagcaacgg    1500
ccaccggccc aacacacacg acttccccct ggggcggcag ctccccacca ggactacccc    1560
tacactgagt cccgaggaac tgctgaacag cagggactgt caccctggcc tgcctcttcc    1620
cccaggattc catcccccatc cggggggccaa ctaccctcct ttcctgccag accagatgca    1680
gtcacaagtc ccctctctcc attatcaaga gctcatgcca ccgggttcct gcctgccaga    1740
ggagcccaag ccaaagaggg gaagaaggtc gtggccccgg aaaagaacag ccacccacac    1800
```

-continued

```
ttgtgactat gcaggctgtg gcaaaaccta taccaagagt tctcatctca aggcacacct      1860
gcgaactcac acaggcgaga aaccttacca ctgtgactgg gacggctgtg ggtggaaatt      1920
cgcccgctcc gatgaactga ccaggcacta ccgcaaacac acagggcacc ggcccttca       1980 gtgccagaag tgtgacaggg cctttccag gtcggaccac cttgccttac acatgaagag      2040 gcactttaa atcccacgta gtggatgtga cccacactgc caggagagag agttcagtat       2100 tttttttct aacctttcac actgtcttcc cacgagggga ggagcccagc tggcaagcgc       2160
tacaatcatg gtcaagttcc cagcaagtca gcttgtgaat ggataatcag gagaaggaa       2220 gagtccaaga gacaaaacag aaatactaaa aacaaacaaa caaaaaaaca aacaaaaaaa      2280
ccaagaaaaa aaaatcacag aacagatggg gtctgatact ggatggatct tctatcattc     2340
caataccaaa tccaacttga acatgcccgg acttacaaaa tgccaagggg tgactggaag      2400
tttgtggata tcagggtata cactaaatca gtgagcttgg ggggagggaa gaccaggatt     2460
cccttgaatt gtgtttcgat gatgcaatac acacgtaaag atcaccttgt atgctctttg      2520
ccttcttaaa aaaaaaagc cattattgtg tcggaggaag aggaagcgat tcaggtacag       2580
aacatgttct aacagcctaa atgatggtgc ttggtgagtt gtggtcctaa aggtaccaaa      2640
cgggggagcc aaagttctcc aactgctgca tactttgac aaggaaaatc tagttttgtc       2700
ttccgatcta cattgatgac ctaagccagg taaataagcc tggtttattt ctgtaacatt      2760
tttatgcaga cagtctgtta tgcactgtgg tttcagatgt gcaataattt gtacaatggt      2820
ttattcccaa gtatgccttt aagcagaaca aatgtgtttt tctatatagt tccttgcctt     2880
aataaatatg taatataaat ttaaccca                                         2908

<210> SEQ ID NO 2
<211> LENGTH: 2639
<212> TYPE: DNA
<213> ORGANISM: Homo sapiens

<400> SEQUENCE: 2
tcgaggcgac cgcgacagtg gtggggacg ctgctgagtg aagagagcg cagcccggcc         60 accggaccta cttactcgcc ttgctgattg tctattttg cgtttacaac ttttctaaga      120
acttttgtat acaaaggaac ttttaaaaa agacgcttcc aagttatatt taatccaaag      180
aagaaggatc tcggccaatt tggggttttg ggtttggct tcgtttcttc tcttcgttga      240 ctttgggggtt caggtgcccc agctgcttcg ggctgccgag gaccttctgg gcccccacat      300
taatgaggca gccacctggc gagtctgaca tggctgtcag cgacgcgctg ctcccatctt      360
tctccacgtt cgcgtctggc ccggcgggaa gggagaagac actgcgtcaa gcaggtgccc      420
cgaataaccg ctggcgggag gagctctccc acatgaagc acttccccca gtgcttcccg      480
gccgccccta tgacctggcg gcggcgaccg tggccacaga cctggagagc ggcggagccg      540
gtgcggcttg cggcggtagc aacctggcgc ccctacctcg gagagagacc gaggagttca      600
acgatctcct ggacctggac tttattctct ccaattcgct gacccatcct ccggagtcag      660
tggccgccac cgtgtcctcg tcagcgtcag cctcctcttc gtcgtcgccg tcgagcagcg      720
gccctgccag cgcgccctcc acctgcagct tcacctatcc gatccgggcc gggaacgacc      780
cgggcgtggc gccggcggc acgggcgag gcctcctcta tggcagggag tccgctcccc        840
ctccgacggc tcccttcaac ctggcggaca tcaacgacgt gagcccctcg gcggcttcg       900 tggccgagct cctgcggcca gaattggacc cggtgtacat tccgccgcag cagccgcagc      960
cgccaggtgg cgggctgatg ggcaagttcg tgctgaaggc gtcgctgagc gcccctggca     1020
```

-continued

```
gcgagtacgg cagcccgtcg gtcatcagcg tcagcaaagg cagccctgac ggcagccacc    1080
cggtggtggt ggcgccctac aacggcgggc cgccgcgcac gtgccccaag atcaagcagg    1140
aggcggtctc ttcgtgcacc cacttgggcg ctggaccccc tctcagcaat ggccaccggc    1200
cggctgcaca cgacttcccc ctggggcggc agctccccag caggactacc ccgaccctgg    1260
gtcttgagga agtgctgagc agcagggact gtcaccctgc cctgccgctt cctcccggct    1320
tccatcccca cccggggccc aattacccat ccttcctgcc cgatcagatg cagccgcaag    1380
tcccgccgct ccattaccaa gagctcatgc cacccggttc ctgcatgcca gaggagccca    1440
agccaaagag gggaagacga tcgtggcccc ggaaaaggac cgccacccac acttgtgatt    1500
acgcgggctg cggcaaaacc tacacaaaga gttcccatct caaggcacac ctgcgaaccc    1560
acacaggtga gaaaccttac cactgtgact gggacggctg tggatggaaa ttcgcccgct    1620
cagatgaact gaccaggcac taccgtaaac acacggggca ccgcccgttc cagtgccaaa    1680
aatgcgaccg agcattttcc aggtcggacc acctcgcctt acacatgaag aggcattttt    1740
aaatcccaga cagtggatat gacccacact gccagaagag aattcagtat ttttttacttt    1800 tcacactgtc ttcccgatga gggaaggagc ccagccagaa agcactacaa tcatggtcaa    1860
gttcccaact gagtcatctt gtgagtggat aatcaggaaa aatgaggaat ccaaaagaca    1920
aaaatcaaag aacagatggg gtctgtgact ggatcttcta tcattccaat tctaaatccg    1980
acttgaatat tcctggactt acaaaatgcc aaggggtga ctggaagttg tggatatcag    2040
ggtataaatt atatccgtga gttgggggag ggaagaccag aattcccttg aattgtgtat    2100
tgatgcaata taagcataaa agatcacctt gtattctctt taccttctaa aagccattat    2160
tatgatgtta gaagaagagg aagaaattca ggtacagaaa acatgtttaa atagcctaaa    2220
tgatggtgct tggtgagtct tggttctaaa ggtaccaaac aaggaagcca agttttcaa     2280 actgctgcat actttgacaa ggaaaatcta tatttgtctt ccgatcaaca tttatgacct    2340
aagtcaggta atatacctgg tttacttctt tagcattttt atgcagacag tctgttatgc    2400
actgtggttt cagatgtgca ataatttgta caatggttta ttcccaagta tgccttaagc    2460
agaacaaatg tgtttttcta tatagttcct tgccttaata aatatgtaat ataaatttaa    2520
gcaaacgtct attttgtata tttgtaaact acaaagtaaa atgaacattt tgtggagttt    2580
gtattttgca tactccaaggt gagaattaag ttttaaataa acctataata ttttatctg    2639
```

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
gagaaggagg cgtggccaac                                                   20